US012648819B2

(12) United States Patent
Ayvali et al.

(10) Patent No.: US 12,648,819 B2
(45) Date of Patent: Jun. 9, 2026

(54) PHASE SEGMENTATION OF A PERCUTANEOUS MEDICAL PROCEDURE

(71) Applicant: Auris Health, Inc., Santa Clara, CA (US)

(72) Inventors: Elif Ayvali, Redwood City, CA (US); Bulat Ibragimov, Copenhagen (DK)

(73) Assignee: Auris Health, Inc., Santa Clara, CA (US)

( * ) Notice: Subject to any disclaimer, the term of this patent is extended or adjusted under 35 U.S.C. 154(b) by 157 days.

(21) Appl. No.: 18/186,124

(22) Filed: Mar. 17, 2023

(65) Prior Publication Data

US 2023/0225802 A1     Jul. 20, 2023

Related U.S. Application Data

(63) Continuation of application No. PCT/IB2022/056506, filed on Jul. 14, 2022.
(Continued)

(51) Int. Cl.
A61B 34/20          (2016.01)
A61B 1/00           (2006.01)
(Continued)

(52) U.S. Cl.
CPC .......... A61B 34/20 (2016.02); A61B 1/00016 (2013.01); A61B 1/307 (2013.01);
(Continued)

(58) Field of Classification Search
CPC ..... A61B 34/20; A61B 1/00016; A61B 1/307; A61B 5/065; A61B 17/3478;
(Continued)

(56) References Cited

U.S. PATENT DOCUMENTS 9,763,741 B2     9/2017  Alvarez et al.
2014/0364728 A1  12/2014  Hashimoto
(Continued)

FOREIGN PATENT DOCUMENTS

CN          108648821 B      12/2020
JP          2014-239767 A    12/2014
(Continued)

OTHER PUBLICATIONS

International Search Report for Appl. No. PCT/IB2022/056506, dated Nov. 1, 2022, 15 pages.
(Continued)

*Primary Examiner* — Bo Joseph Peng
(74) *Attorney, Agent, or Firm* — Paradice & Li LLP

(57)                    ABSTRACT

Techniques for segmenting a percutaneous medical procedure based on one or more determinable phases. The techniques may include obtaining a first set of features over a first time period. The first set of features may be derived from instrument telemetry data corresponding to an endoluminal scope instrument. The technique may also include obtaining a second set of features over the first time period. The second set of features may be derived from instrument telemetry data corresponding to a percutaneous needle instrument. Based on the first set of features and the second set of features, the techniques may classify at least a portion of the first time period as a first phase of the percutaneous medical procedure.

20 Claims, 16 Drawing Sheets

Related U.S. Application Data

(60) Provisional application No. 63/223,340, filed on Jul. 19, 2021.

(51) Int. Cl.

| | |
|---|---|
| *A61B 1/307* | (2006.01) |
| *A61B 5/06* | (2006.01) |
| *A61B 17/34* | (2006.01) |
| *G16H 10/60* | (2018.01) |
| *G16H 40/20* | (2018.01) |
| *A61B 34/30* | (2016.01) |

(52) U.S. Cl.
CPC .......... *A61B 5/065* (2013.01); *A61B 17/3478* (2013.01); *G16H 10/60* (2018.01); *G16H 40/20* (2018.01); *A61B 2034/303* (2016.02)

(58) Field of Classification Search
CPC .............. A61B 2034/303; A61B 34/25; A61B 2017/00207; A61B 2034/105; A61B 2034/107; A61B 2034/2048; A61B 2034/2051; A61B 2034/2059; A61B 2034/2061; A61B 2034/2065; A61B 2034/252; A61B 2034/254; A61B 2090/376; A61B 34/30; A61B 34/00; G16H 10/60; G16H 40/20; G16H 50/70; G16H 15/00; G16H 30/20; G16H 40/67; G16H 40/63; G16H 20/40; G16H 30/40; G16H 50/20; G06N 3/0442; G06N 3/0464; G06N 3/09; G06N 7/01

See application file for complete search history.

(56) References Cited

U.S. PATENT DOCUMENTS

| | | | |
|---|---|---|---|
| 2019/0206563 A1 | 7/2019 | Shelton, IV et al. |
| 2019/0262084 A1 | 8/2019 | Roh et al. |
| 2019/0325574 A1* | 10/2019 | Jin ...................... G06V 10/751 |
| 2019/0337152 A1* | 11/2019 | Homberg .............. B25J 9/1697 |
| 2020/0100855 A1* | 4/2020 | Leparmentier ........ A61B 34/30 |
| 2021/0012868 A1 | 1/2021 | Wolf et al. |
| 2021/0186634 A1 | 6/2021 | Jarc et al. |
| 2021/0196312 A1 | 7/2021 | Plewe et al. |

FOREIGN PATENT DOCUMENTS

| | | |
|---|---|---|
| WO | 2020036968 A1 | 2/2020 |
| WO | 2020056086 A1 | 3/2020 |
| WO | 2020142338 A1 | 7/2020 |

OTHER PUBLICATIONS

Written Opinion for Appl. No. PCT/IB2022/056506, dated Nov. 1, 2022, 4 pages.
Bardram et al., "Phase Recognition During Surgical Procedures Using Embedded and Body-Worn sensors," 2011 IEEE International Conference on Pervasive Computing and Communications, PerCom (2011) pp. 45-53.
European Search Report and Opinion from Application No. 22845523.4, dated Apr. 29, 2025, pp. 1-17.
Holden et al., "Feasibility of Real-Time Workflow Segmentation for Tracked Needle Interventions," in IEEE Transactions on Biomedical Engineering, vol. 61, No. 6, pp. 1720-1728, Jun. 2014.
Ibragimov, B., Zhen, J., & Ayvali, E. (2023). Deep learning for detection of clinical operations in robot-assisted percutaneous renal access. IEEE Access, 11, 90358-90366. https://doi.org/10.1109/ACCESS.2023.3305246.
Supplementary European Search Report and Opinion from Application No. 22845523.4, dated Aug. 7, 2025, pp. 1-22.
International Preliminary Report on Patentability for Appl. No. PCT/IB2022/056506, dated Jan. 18, 2024, 5 pages.
Office Action from Japan Patent Application No. 2024-503445, proposed date: Jan. 29, 2026, 11 pages.

* cited by examiner

*MANY-TO-MANY APPROACH*

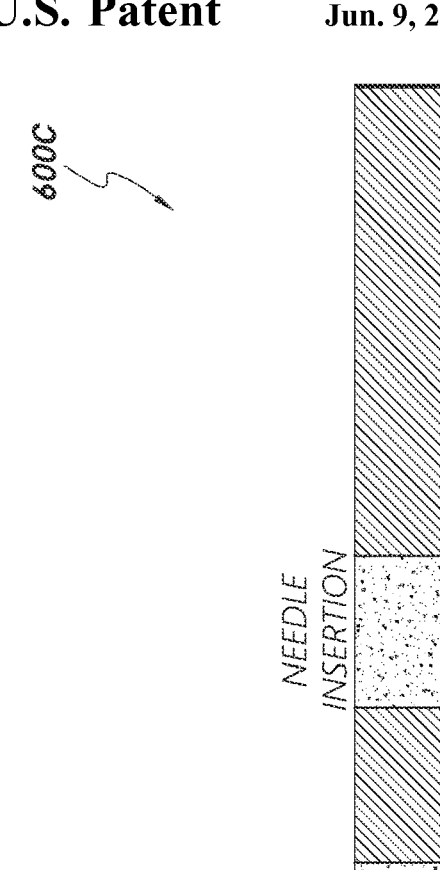
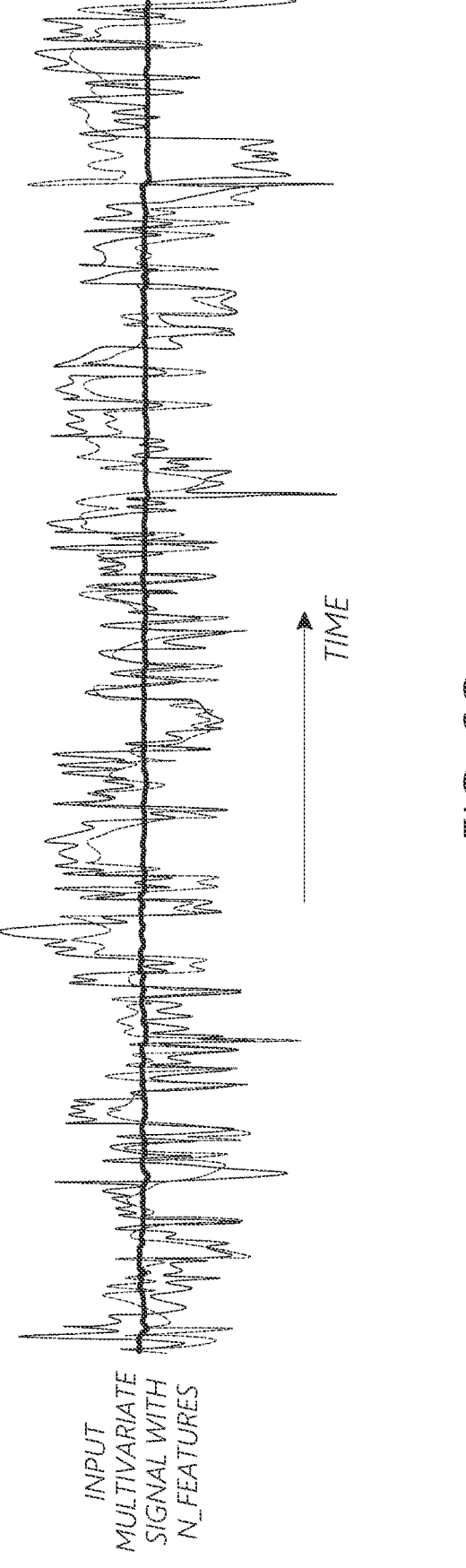
*FIG. 6C*

*700*

*710*
OBTAIN A FIRST SET OF FEATURES OVER
A FIRST TIME PERIOD

*720*
OBTAIN A SECOND SET OF FEATURES
OVER THE FIRST TIME PERIOD

*730*
CLASSIFY THE FIRST TIME PERIOD AS A
FIRST PHASE OF THE PERCUTANEOUS
MEDICAL PROCEDURE BASED ON THE
FIRST SET OF FEATURES AND THE
SECOND SET OF FEATURES

*800*

OBTAIN TELEMETRY DATA FROM ONE OR MORE CASE LOGS OF A FIRST PERCUTANEOUS PROCEDURE          *810*

CLASSIFY A FIRST TIME PERIOD ASSOCIATED WITH THE TELEMETRY DATA WITH A FIRST PHASE OF THE PERCUTANEOUS PROCEDURE BASED ON THE TELEMETRY DATA          *820*

GENERATE CLINICAL METRICS ASSOCIATED THE FIRST PHASE IN THE PERCUTANEOUS PROCEDURE FROM TELEMETRY DATA CORRESPONDING TO THE FIRST TIME PERIOD          *830*

PHASE SEGMENTATION OF A PERCUTANEOUS MEDICAL PROCEDURE

CROSS REFERENCE TO PRIOR APPLICATION

This application is a continuation of International Patent Application No. PCT/IB2022/056506, filed Jul. 14, 2022, entitled PHASE SEGMENTATION OF A PERCUTANEOUS MEDICAL PROCEDURE, which claims priority to U.S. Provisional Patent Application No. 63/223,340, entitled PHASE SEGMENTATION OF A PERCUTANEOUS MEDICAL PROCEDURE, filed Jul. 19, 2021, the disclosures of which are hereby incorporated by reference in their entirety for all purposes.

BACKGROUND

Field

The present disclosure relates to the field of medical procedures.

Description of the Related Art

Various medical procedures involve the use of one or more devices configured to penetrate the human anatomy to reach a treatment site. Certain operational processes can involve inserting the one or more devices through the skin and other anatomy of a patient to reach the treatment site and extract an object from the patient, such as a urinary stone.

BRIEF DESCRIPTION OF THE DRAWINGS

Various embodiments are depicted in the accompanying drawings for illustrative purposes and should in no way be interpreted as limiting the scope of the disclosure. In addition, various features of different disclosed embodiments can be combined to form additional embodiments, which are part of this disclosure. Throughout the drawings, reference numbers may be reused to indicate correspondence between reference elements.

FIG. 6C is a diagram showing a binary classification approach that a segmentation module may incorporate in accordance with one or more embodiments.

FIG. 8 is a flowchart showing a method to generate clinical metrics in a percutaneous medical procedure, according to an example embodiment.

FIG. 10 is a diagram illustrating example guidance that may be provided according to example embodiments.

DETAILED DESCRIPTION

Figure 1:
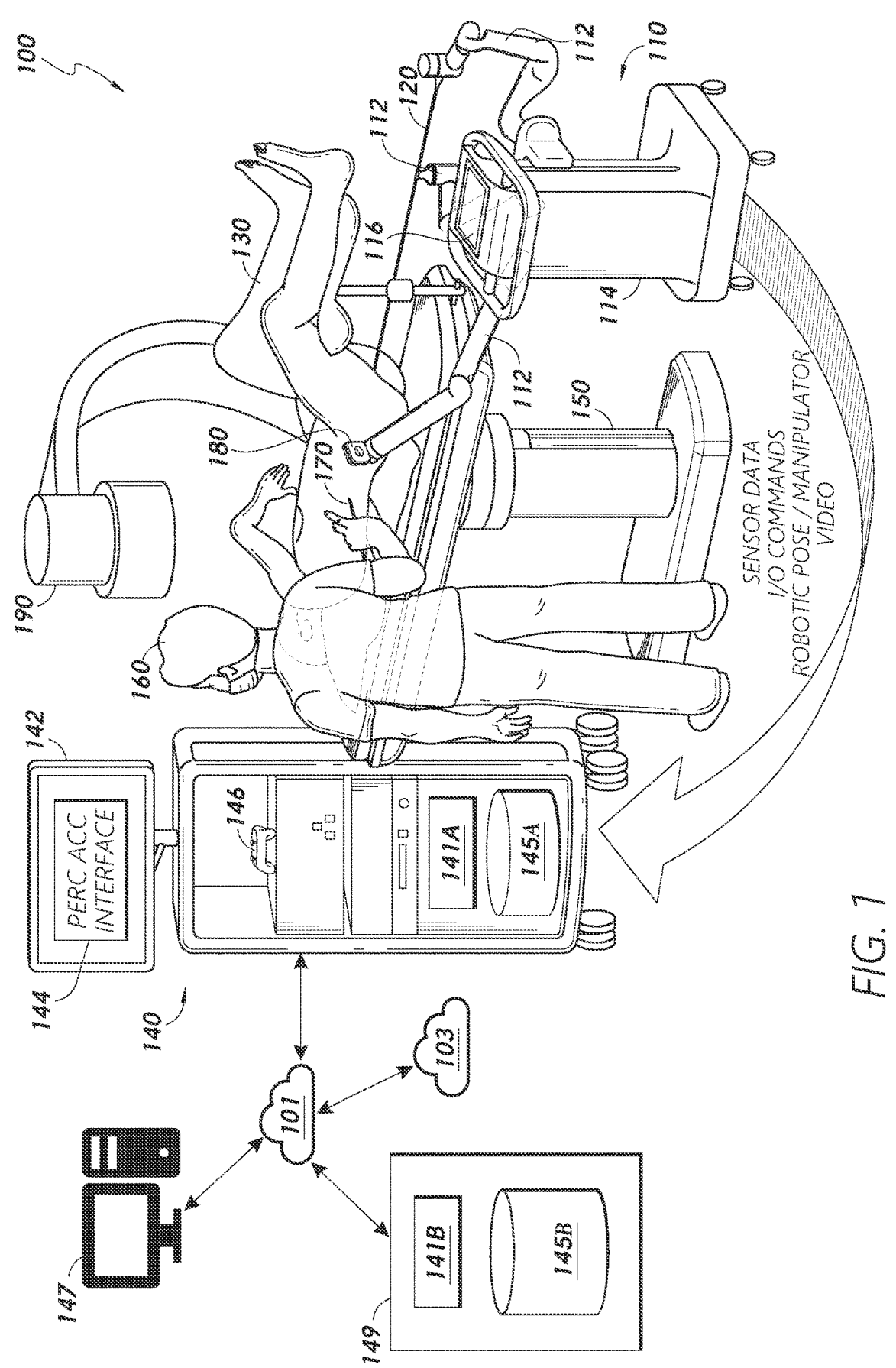
FIG. 1 illustrates an embodiment of a medical system configured to implement the techniques discussed herein in accordance with one or more embodiments.

The headings provided herein are for convenience only and do not necessarily affect the scope or meaning of disclosure. Although certain exemplary embodiments are disclosed below, the subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location may be used herein to refer to the anatomy of animals, and namely humans, with respect to the exemplary embodiments. Although certain spatially relative terms, such as "outer," "inner," "upper," "lower," "below," "above," "vertical," "horizontal," "top," "bottom," and similar terms, are used herein to describe a spatial relationship of one device/ element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Overview

The present disclosure relates to systems, devices, and methods to segment a medical procedure according to determinable phases. In exemplary embodiments, this segmentation is done based on case logs generated by a medical system performing or having performed a percutaneous medical procedure, or any other suitable medical procedure. Although certain aspects of the present disclosure are described in detail herein in the context of renal, urological, and/or nephrological procedures, such as kidney stone removal/treatment procedures, it should be understood that such context is provided for convenience and clarity, and the concepts disclosed herein are applicable to any suitable medical procedure. However, as mentioned, description of the renal/urinary anatomy and associated medical issues and procedures is presented below to aid in the description of the concepts disclosed herein.

Kidney stone disease, also known as urolithiasis, is a relatively common medical condition that involves the formation, in the urinary tract, of a solid piece of material, referred to as "kidney stones," "urinary stones," "renal calculi," "renal lithiasis," or "nephrolithiasis." Urinary stones can be formed and/or found in the kidneys, the ureters, and the bladder (referred to as "bladder stones"). Such urinary stones form as a result of concentrated minerals and can cause significant abdominal pain once they reach a size sufficient to impede urine flow through the ureter or urethra. Urinary stones can be formed from calcium, magnesium, ammonia, uric acid, cysteine, and/or other compounds.

To remove urinary stones from the bladder and ureter, surgeons can insert a ureteroscope into the urinary tract through the urethra. Typically, a ureteroscope includes an endoscope at its distal end configured to enable visualization of the urinary tract. The ureteroscope can also include a lithotomy mechanism to capture or break apart urinary stones. During a ureteroscopy procedure, one physician/technician can control the position of the ureteroscope, while another other physician/technician can control the lithotomy mechanism.

In order to remove relatively large stones from the kidneys (i.e., "kidney stones"), physicians can use a percutaneous nephrolithotomy ("PCNL") technique that includes inserting a nephroscope through the skin to break up and/or remove the stone(s). Locating the kidney stone(s) can be achieved using fluoroscopy to provide a target for insertion of the nephroscope. However, fluoroscopy increases the cost of the nephrolithotomy procedure due to the cost of the fluoroscope itself as well as the cost of a technician to operate the fluoroscope. Fluoroscopy also exposes the patient to radiation for a prolonged period of time. Even with fluoroscopy, accurately making a percutaneous incision to access the kidney stone can be difficult and undesirably imprecise. Furthermore, some nephrolithotomy techniques involve a two-day or three-day in-patient stay. In sum, certain nephrolithotomy techniques can be relatively costly and problematic for patients.

In some implementations, the present disclosure relates to techniques and systems to segment a medical procedure according to determinable phases based on case logs generated by a medical system performing or having performed a percutaneous medical procedure, or any other suitable medical procedure. As used herein, "case logs" may refer to the runtime data a medical system generates or collects during the operation. In some circumstances, case logs may alternately or additionally include pre- or post-operation data, whether actively generated or collected by the system or manually input into or transferred to the system. It is to be appreciated that the term case logs does not necessarily imply any particular data storage format and some embodiments may simply store the case logs as raw sensor data. Other embodiments structure the case logs into a specified or determinable file format. The term case logs may alternatively be referred to herein as "case data." Case logs may include data representing the poses of the instruments of the medical system, poses of the robotic arms or manipulators of the medical system, user interface ("UI") commands, system status, video data, audio data, and the like. However, such data does not directly provide clinical metrics for evaluating the success of the medical procedure or the performance of the physician, providing intraoperative recommendations or insights, or performing automated actions. For example, the case logs, without segmentation, do not identify when needle insertion starts or how many stick attempts a user makes after selecting a target location for entering into the kidney (see, e.g., in greater detail below). Further, case logs may fail to have information on, e.g., what insertion site the user has selected, a length between a patient's skin and a target (either a position identified by the physician (e.g., see tagging below), or an estimate of the calyx/papilla wall) within the calyx/papilla (such a length may be referred to as tract length).

Accordingly, once a medical procedure has been segmented according to determinable medical procedure phases, embodiments may analyze the case data in the context of the segmentation to, among other things, generate phase specific metrics, provide recommendations and insights, and perform automated actions. For example, to be able to compute a tract length, a system may first calculate a position of the needle tip at the time the user selects an insertion site on the skin and a target position of the calyx/papilla (or representation thereof). However, some of these phase specific metrics are only computable from the case logs after segmenting the percutaneous medical procedure. Portions of this disclosure focus on systems, methods, and apparatuses for recognizing or otherwise identifying what phase is going on in a procedure at a given time, so that an exemplary system, method, or apparatus can compute clinical metrics and calculate how long each or any phase of the procedure takes. Example metrics that may be determined by embodiments contemplated herein are described in greater detail below. Further, embodiments contemplated herein may also analyze the clinical metrics to determine correlations between the metrics and procedure success. These correlations can be used to provide guidance and insights before, during, and after procedures.

In many embodiments, the techniques and systems described herein are discussed in the context of a percutaneous procedure, which can include any procedure where access is gained to a target location by making a puncture and/or incision in the skin, mucous membrane, and/or other body layer. However, it should be understood that these techniques and systems can be implemented in the context of any medical procedure including, for example, minimally invasive procedures (e.g., a laparoscopy), non-invasive procedures (e.g., an endoscopy), therapeutic procedures, diagnostic procedures, percutaneous procedures, non-percutaneous procedures, or other types of procedures. An endoscopic procedure can include a bronchoscopy, a ureteroscopy, a gastroscopy, nephroscopy, nephrolithotomy, and so on. In some embodiments, in the context of a laparoscopic procedure or another procedure, the techniques and systems described herein can be used to generate phase specific metrics for procedures that involve aligning a first medical instrument to a second medical instrument/anatomical position, such as to guide port placement (e.g., to align a first trocar to a second trocar/anatomical position). Further, in some embodiments, in the context of a diagnostic procedure, these techniques and systems can be used to segment a medical procedure involving alignment of an ultrasound probe equipped with an electromagnetic sensor to an anatomical target or to guide a user to a set of target orientations to reconstruct anatomy, such as three-dimensional (3D) kidney anatomy. Moreover, in some embodiments, in the context of an endoscopic procedure, the techniques and systems can be used to segment a medical procedure involving guided positioning of a bronchoscope while performing a biopsy at a marked location, such as a location of a tumor.

Medical System

FIG. 1 illustrates an example medical system 100 for performing various medical procedures in accordance with aspects of the present disclosure. The medical system 100 includes a robotic system 110 configured to engage with and/or control a medical instrument to perform a procedure on a patient 130. The medical system 100 also includes a control system 140 configured to interface with the robotic system 110, provide information regarding the procedure, and/or perform a variety of other operations. For example, the control system 140 can include a display(s) 142 to present certain information to assist the physician 160. The display(s) 142 may be a monitor, screen, television, virtual reality hardware, augmented reality hardware, three-dimensional imaging devices (e.g., hologram devices) and the like, or combinations thereof. The medical system 100 can include a table 150 configured to hold the patient 130. The system 100 can further include an electromagnetic (EM) field generator 180, which can be held by one or more robotic arms 112 of the robotic system 110 or can be a stand-alone device. In examples, the medical system 100 can also include an imaging device 190 which can be integrated into a C-arm and/or configured to provide imaging during a procedure, such as for a fluoroscopy-type procedure. Although shown in FIG. 1, in some embodiments the imaging device 190 is eliminated.

In some implementations, the medical system 100 can be used to perform a percutaneous procedure. For example, if the patient 130 has a kidney stone that is too large to be removed through a urinary tract, the physician 160 can perform a procedure to remove the kidney stone through a percutaneous access point on the patient 130. To illustrate, the physician 160 can interact with the control system 140 to control the robotic system 110 to advance and navigate the medical instrument (e.g., a scope) from the urethra, through the bladder, up the ureter, and into the kidney where the stone is located. The control system 140 can provide information via the display(s) 142 regarding the medical instrument to assist the physician 160 in navigating the medical instrument, such as real-time images captured therewith.

Once at the site of the kidney stone (e.g., within a calyx of the kidney), the medical instrument can be used to designate/tag a target location for the medical instrument (e.g., a needle) to access the kidney percutaneously (e.g., a desired point to access the kidney). To minimize damage to the kidney and/or the surrounding anatomy, the physician 160 can designate a particular papilla as the target location for entering into the kidney with the medical instrument. However, other target locations can be designated or determined. To assist the physician in driving the medical instrument into the patient 130 through the particular papilla, the control system 140 can provide a percutaneous access interface 144, which can include a visualization to indicate an alignment of an orientation of the medical instrument relative to a target trajectory (e.g., a desired access path from the patient's skin to the target location), a visualization to indicate a progress of inserting the medical instrument into the kidney towards the target location, guidance on the percutaneous procedure, and/or other information. Once the medical instrument has reached the target location (as determined, e.g., by sensors attached to the needle 170, the scope 120, or other any sensor or imaging modality), the physician 160 can use the medical instrument and/or another medical instrument to extract the kidney stone from the patient 130, such as through the percutaneous access point.

Although the above percutaneous procedure and/or other procedures are discussed in the context of using the medical instrument, in some implementations a percutaneous procedure can be performed without the assistance of the medical instrument. Further, the medical system 100 can be used to perform a variety of other procedures.

Moreover, although many embodiments describe the physician 160 using the medical instrument, the medical instrument can alternatively be used by a component of the medical system 100. For example, the medical instrument can be held/manipulated by the robotic system 110 (e.g., the one or more robotic arms 112) and the techniques discussed herein can be implemented to control the robotic system 110 to insert the medical instrument with the appropriate pose (or aspect of a pose, such as orientation or position) to reach a target location.

In the example of FIG. 1, the medical instrument is implemented as a scope 120 and the medical instrument is implemented as a needle 170. Thus, for ease of discussion, the medical instrument is referred to as "the scope 120" or "the lumen-based medical instrument," and the medical instrument is referred to as "the needle 170" or "the percutaneous medical instrument." However, the medical instrument and the medical instrument can each be implemented as a suitable type of medical instrument including, for example, a scope (sometimes referred to as an "endoscope"), a needle, a catheter, a guidewire, a lithotripter, a basket retrieval device, forceps, a vacuum, a needle, a scalpel, an imaging probe, jaws, scissors, graspers, needle holder, micro dissector, staple applier, tacker, suction/irrigation tool, clip applier, and so on. In some embodiments, a medical instrument is a steerable device, while other embodiments a medical instrument is a non-steerable device. In some embodiments, a surgical tool refers to a device that is configured to puncture or to be inserted through the human anatomy, such as a needle, a scalpel, a guidewire, and so on. However, a surgical tool can refer to other types of medical instruments.

In some embodiments, a medical instrument, such as the scope 120 and/or the needle 170, includes a sensor that is configured to generate sensor data, which can be sent to another device. In examples, sensor data can indicate a location/orientation of the medical instrument and/or can be used to determine a location/orientation of the medical instrument. For instance, a sensor can include an electromagnetic (EM) sensor with a coil of conductive material. Here, an EM field generator, such as the EM field generator

180, can provide an EM field that is detected by the EM sensor on the medical instrument. The magnetic field can induce small currents in coils of the EM sensor, which can be analyzed to determine a distance and/or angle/orientation between the EM sensor and the EM field generator. Further, a medical instrument can include other types of sensors configured to generate sensor data, such as one or more of any of: a camera, a range sensor, a radar device, a shape sensing fiber, an accelerometer, a gyroscope, a satellite-based positioning sensor (e.g., a global positioning system (GPS)), a radio-frequency transceiver, and so on. In some embodiments, a sensor is positioned on a distal end of a medical instrument, while in other embodiments a sensor is positioned at another location on the medical instrument. In some embodiments, a sensor on a medical instrument can provide sensor data to the control system 140 and the control system 140 can perform one or more localization techniques to determine/track a position and/or an orientation of a medical instrument.

In some embodiments, the medical system 100 may record or otherwise track the runtime data that is generated during a medical procedure. For example, the medical system 100 may track or otherwise record the sensor readings (e.g., sensor data) from the instruments (e.g., the scope 120 and the needle 170) in case data store 145A (e.g., a computer storage system, such as computer readable memory, database, filesystem, and the like). In addition to sensor data, the medical system 100 can store other types of case logs in the case data store 145A. For example, in the context of FIG. 1, the case logs can include time series data of the video images captured by the scope 120, status of the robotic system 110, commanded data from an I/O device(s) (e.g., I/O device(s) 146 discussed below), audio data (e.g., as may be captured by audio capturing devices embedded in the medical system 100, such as microphones on the medical instruments, robotic arms, or elsewhere in the medical system), external (relative to the patient) imaging device (such as RGB cameras, LIDAR imaging sensors, fluoroscope imaging sensors, etc.) and the like.

As shown in FIG. 1, the control system 140 includes an analytics engine 141A which may operate on the case logs stored in the case data store 145A to label the case logs according to a procedure phase for a given time. As is discussed in greater detail below, the analytics engine 141A may employ machine learning techniques to segment the medical procedure according to the different phases. In some embodiments, once the medical procedure has been segmented, the analytics engine 141A may generate metrics for the medical procedure phases, the medical procedure generally, or provide insights and recommendations to the users of the medical system 100 (e.g., physicians, staff, training personnel, and the like).

FIG. 1 further shows that in some embodiments the control system 140 may include a network connection (e.g., via network 101) to a cloud-based data analytics platform 149. The cloud-based data analytics platform 149 may be a computer system that provides third party computers 147 postoperative analytic capabilities on a given medical procedure or analytics across multiple medical procedures. As shown in FIG. 1, the cloud-based data analytics platform 149 may further connect to additional medical systems 103, which each in turn may transmit case logs to the cloud-based data analytics platform 149. Because the cloud-based data analytics platform receives case logs from multiple medical systems, the cloud-based data analytics platform 149 may have access to a comparatively larger pool of data than a single medical system would have access to and may in turn aggregate the case logs across multiple medical systems to derive medical procedure insights. Medical procedure insights may include guidance on factors that result in an increased likelihood for success in a medical procedure based on the metrics derived from segmenting the case logs across medical systems and across medical procedures. Segmentation of case logs is discussed in greater detail below.

As shown in FIG. 1, the cloud-based data analytics platform 149 may include an analytics engine 141B and cloud-based data store 145B. The cloud-based data store 145B may be a computer storage device that stores the system data records from the medical system 100 and the additional medical systems 103. The analytics engine 141B may include features and capabilities similar to the analytics engine 141A. However, in some embodiments, the analytics engine 141A may further operate to analyze case logs across multiple medical systems (e.g., medical system 100 and medical systems 103) to generate metrics or insights. This may provide comparatively robust insights because the data used to generate such metrics or insights is using a broader range of information. Additionally or alternatively, the cloud-based analytics engine 141B may uses machine learning techniques that are suitable for post-operative classification, whereas the local analytics engine 141B may use machine learning techniques that are suitable for real-time or near-real time classification. These machine learning techniques are described in greater detail below.

The term "scope" or "endoscope" are used herein according to their broad and ordinary meanings and can refer to any type of elongate medical instrument having image generating, viewing, and/or capturing functionality and configured to be introduced into any type of organ, cavity, lumen, chamber, and/or space of a body. For example, references herein to scopes or endoscopes can refer to a ureteroscope (e.g., for accessing the urinary tract), a laparoscope, a nephroscope (e.g., for accessing the kidneys), a bronchoscope (e.g., for accessing an airway, such as the bronchus), a colonoscope (e.g., for accessing the colon), an arthroscope (e.g., for accessing a joint), a cystoscope (e.g., for accessing the bladder), a borescope, and so on.

A scope can comprise a tubular and/or flexible medical instrument that is configured to be inserted into the anatomy of a patient to capture images of the anatomy. In some embodiments, a scope can accommodate wires and/or optical fibers to transfer signals to/from an optical assembly and a distal end of the scope, which can include an imaging device, such as an optical camera. The camera/imaging device can be used to capture images of an internal anatomical space, such as a target calyx/papilla of a kidney. A scope can further be configured to accommodate optical fibers to carry light from proximately-located light sources, such as light-emitting diodes, to the distal end of the scope. The distal end of the scope can include ports for light sources to illuminate an anatomical space when using the camera/imaging device. In some embodiments, the scope is configured to be controlled by a robotic system, such as the robotic system 110. The imaging device can comprise an optical fiber, fiber array, and/or lens. The optical components can move along with the tip of the scope such that movement of the tip of the scope results in changes to the images captured by the imaging device.

A scope can be articulable, such as with respect to at least a distal portion of the scope, so that the scope can be steered within the human anatomy. In some embodiments, a scope is configured to be articulated with, for example, five or six degrees of freedom, including X, Y, Z coordinate movement, as well as pitch, yaw, and roll. A position sensor(s) of the scope can likewise have similar degrees of freedom with respect to the position information they produce/provide. A scope can include telescoping parts, such as an inner leader portion and an outer sheath portion, which can be manipulated to telescopically extend the scope. A scope, in some instances, can comprise a rigid or flexible tube, and can be dimensioned to be passed within an outer sheath, catheter, introducer, or other lumen-type device, or can be used without such devices. In some embodiments, a scope includes a working channel for deploying medical instruments (e.g., lithotripters, basketing devices, forceps, etc.), irrigation, and/or aspiration to an operative region at a distal end of the scope.

The robotic system 110 can be configured to at least partly facilitate execution of a medical procedure. The robotic system 110 can be arranged in a variety of ways depending on the particular procedure. The robotic system 110 can include the one or more robotic arms 112 configured to engage with and/or control the scope 120 to perform a procedure. As shown, each robotic arm 112 can include multiple arm segments coupled to joints, which can provide multiple degrees of movement. In the example of FIG. 1, the robotic system 110 is positioned proximate to the patient's 130 legs and the robotic arms 112 are actuated to engage with and position the scope 120 for access into an access point, such as the urethra of the patient 130. When the robotic system 110 is properly positioned, the scope 120 can be inserted into the patient 130 robotically using the robotic arms 112, manually by the physician 160, or a combination thereof. The robotic arms 112 can also be connected to the EM field generator 180, which can be positioned near a treatment site, such as within proximity to the kidneys of the patient 130.

The robotic system 110 can also include a support structure 114 coupled to the one or more robotic arms 112. The support structure 114 can include control electronics/circuitry, one or more power sources, one or more pneumatics, one or more optical sources, one or more actuators (e.g., motors to move the one or more robotic arms 112), memory/data storage, and/or one or more communication interfaces. In some embodiments, the support structure 114 includes an input/output (I/O) device(s) 116 configured to receive input, such as user input to control the robotic system 110, and/or provide output, such as a graphical user interface (GUI), information regarding the robotic system 110, information regarding a procedure, and so on. The I/O device(s) 116 can include a display, a touchscreen, a touchpad, a projector, a mouse, a keyboard, a microphone, a speaker, etc. In some embodiments, the robotic system 110 is movable (e.g., the support structure 114 includes wheels) so that the robotic system 110 can be positioned in a location that is appropriate or desired for a procedure. In other embodiments, the robotic system 110 is a stationary system. Further, in some embodiments, the robotic system 110 is integrated into the table 150.

The robotic system 110 can be coupled to any component of the medical system 100, such as the control system 140, the table 150, the EM field generator 180, the scope 120, and/or the needle 170. In some embodiments, the robotic system is communicatively coupled to the control system 140. In one example, the robotic system 110 can be configured to receive a control signal from the control system 140 to perform an operation, such as to position a robotic arm 112 in a particular manner, manipulate the scope 120, and so on. In response, the robotic system 110 can control a component of the robotic system 110 to perform the operation. In another example, the robotic system 110 is configured to receive an image from the scope 120 depicting internal anatomy of the patient 130 and/or send the image to the control system 140, which can then be displayed on the display(s) 142. Furthermore, in some embodiments, the robotic system 110 is coupled to a component of the medical system 100, such as the control system 140, in such a manner as to allow for fluids, optics, power, or the like to be received therefrom. Example details of the robotic system 110 are discussed in further detail below in reference to FIG. 12.

The control system 140 can be configured to provide various functionality to assist in performing a medical procedure. In some embodiments, the control system 140 can be coupled to the robotic system 110 and operate in cooperation with the robotic system 110 to perform a medical procedure on the patient 130. For example, the control system 140 can communicate with the robotic system 110 via a wireless or wired connection (e.g., to control the robotic system 110 and/or the scope 120, receive an image(s) captured by the scope 120, etc.), provide fluids to the robotic system 110 via one or more fluid channels, provide power to the robotic system 110 via one or more electrical connections, provide optics to the robotic system 110 via one or more optical fibers or other components, and so on. Further, in some embodiments, the control system 140 can communicate with the needle 170 and/or the scope 120 to receive sensor data from the needle 170 and/or the scope 120 (via the robotic system 110 and/or directly from the needle 170 and/or the scope 120). Moreover, in some embodiments, the control system 140 can communicate with the table 150 to position the table 150 in a particular orientation or otherwise control the table 150. Further, in some embodiments, the control system 140 can communicate with the EM field generator 180 to control generation of an EM field around the patient 130.

The control system 140 includes various I/O devices configured to assist the physician 160 or others in performing a medical procedure. In this example, the control system 140 includes an I/O device(s) 146 that is employed by the physician 160 or other user to control the scope 120, such as to navigate the scope 120 within the patient 130. For example, the physician 160 can provide input via the I/O device(s) 146 and, in response, the control system 140 can send control signals to the robotic system 110 to manipulate the scope 120. Although the I/O device(s) 146 is illustrated as a controller in the example of FIG. 1, the I/O device(s) 146 can be implemented as a variety of types of I/O devices, such as a touchscreen, a touch pad, a mouse, a keyboard, a surgeon or physician console, virtual reality hardware, augmented hardware, microphone, speakers, haptic devices, and the like.

As also shown in FIG. 1, the control system 140 can include the display(s) 142 to provide various information regarding a procedure. As noted above, the display(s) 142 can present the percutaneous access interface 144 to assist the physician 160 in the percutaneous access procedure (e.g., manipulating the needle 170 towards a target site). The display(s) 142 can also provide (e.g., via the percutaneous access interface 144 and/or another interface) information regarding the scope 120. For example, the control system 140 can receive real-time images that are captured by the scope 120 and display the real-time images via the display(s) 142. Additionally or alternatively, the control system 140 can receive signals (e.g., analog, digital, electrical, acoustic/sonic, pneumatic, tactile, hydraulic, etc.) from a medical monitor and/or a sensor associated with the patient 130, and the display(s) 142 can present information regarding the health or environment of the patient 130. Such information can include information that is displayed via a medical monitor including, for example, a heart rate (e.g., ECG, HRV, etc.), blood pressure/rate, muscle bio-signals (e.g., EMG), body temperature, blood oxygen saturation (e.g., SpO2), CO2, brainwaves (e.g., EEG), environmental and/or local or core body temperature, and so on.

To facilitate the functionality of the control system 140, the control system 140 can include various components (sometimes referred to as "subsystems"). For example, the control system 140 can include control electronics/circuitry, as well as one or more power sources, pneumatics, optical sources, actuators, memory/data storage devices, and/or communication interfaces. In some embodiments, the control system 140 includes control circuitry comprising a computer-based control system that is configured to store executable instructions, that when executed, cause various operations to be implemented. In some embodiments, the control system 140 is movable, such as that shown in FIG. 1, while in other embodiments, the control system 140 is a stationary system. Although various functionality and components are discussed as being implemented by the control system 140, any of this functionality and/or components can be integrated into and/or performed by other systems and/or devices, such as the robotic system 110, the table 150, and/or the EM field generator 180 (or even the scope 120 and/or the needle 170). Example details of the control system 140 are discussed in further detail below in reference to FIG. 13.

The imaging device 190 can be configured to capture/generate one or more images of the patient 130 during a procedure, such as one or more x-ray or CT images. In examples, images from the imaging device 190 can be provided in real-time to view anatomy and/or medical instruments, such as the scope 120 and/or the needle 170, within the patient 130 to assist the physician 160 in performing a procedure. The imaging device 190 can be used to perform a fluoroscopy (e.g., with a contrast dye within the patient 130) or another type of imaging technique. Although shown in FIG. 1, in many embodiments the imaging device 190 is not implemented for performing a procedure and/or the imaging device 190 (including the C-arm) is eliminated.

The various components of the medical system 100 can be communicatively coupled to each other over a network, which can include a wireless and/or wired network. Example networks include one or more personal area networks (PANs), local area networks (LANs), wide area networks (WANs), Internet area networks (IANs), cellular networks, the Internet, etc. Further, in some embodiments, the components of the medical system 100 are connected for data communication, fluid/gas exchange, power exchange, and so on, via one or more support cables, tubes, or the like.

The medical system 100 can provide a variety of benefits, such as providing guidance to assist a physician in performing a procedure (e.g., instrument tracking, instrument alignment information, etc.), enabling a physician to perform a procedure from an ergonomic position without the need for awkward arm motions and/or positions, enabling a single physician to perform a procedure with one or more medical instruments, avoiding radiation exposure (e.g., associated with fluoroscopy techniques), enabling a procedure to be performed in a single-operative setting, providing continuous suction to remove an object more efficiently (e.g., to remove a kidney stone), and so on. For example, the medical system 100 can provide guidance information to assist a physician in using various medical instruments to access a target anatomical feature while minimizing bleeding and/or damage to anatomy (e.g., critical organs, blood vessels, etc.). Further, the medical system 100 can provide non-radiation-based navigational and/or localization techniques to reduce physician and patient exposure to radiation and/or reduce the amount of equipment in the operating room. Moreover, the medical system 100 can provide functionality that is distributed between at least the control system 140 and the robotic system 110, which can be independently movable. Such distribution of functionality and/or mobility can enable the control system 140 and/or the robotic system 110 to be placed at locations that are optimal for a particular medical procedure, which can maximize working area around the patient and/or provide an optimized location for a physician to perform a procedure.

Although various techniques and systems are discussed as being implemented as robotically-assisted procedures (e.g., procedures that at least partly use the medical system 100), the techniques and systems can be implemented in other procedures, such as in fully-robotic medical procedures, human-only procedures (e.g., free of robotic systems), and so on. For example, the medical system 100 can be used to perform a procedure without a physician holding/manipulating a medical instrument (e.g., a fully-robotic procedure). That is, medical instruments that are used during a procedure, such as the scope 120 and the needle 170, can each be held/controlled by components of the medical system 100, such as the robotic arm(s) 112 of the robotic system 110.

Example Percutaneous Procedure Using a Medical System

Figure 2:
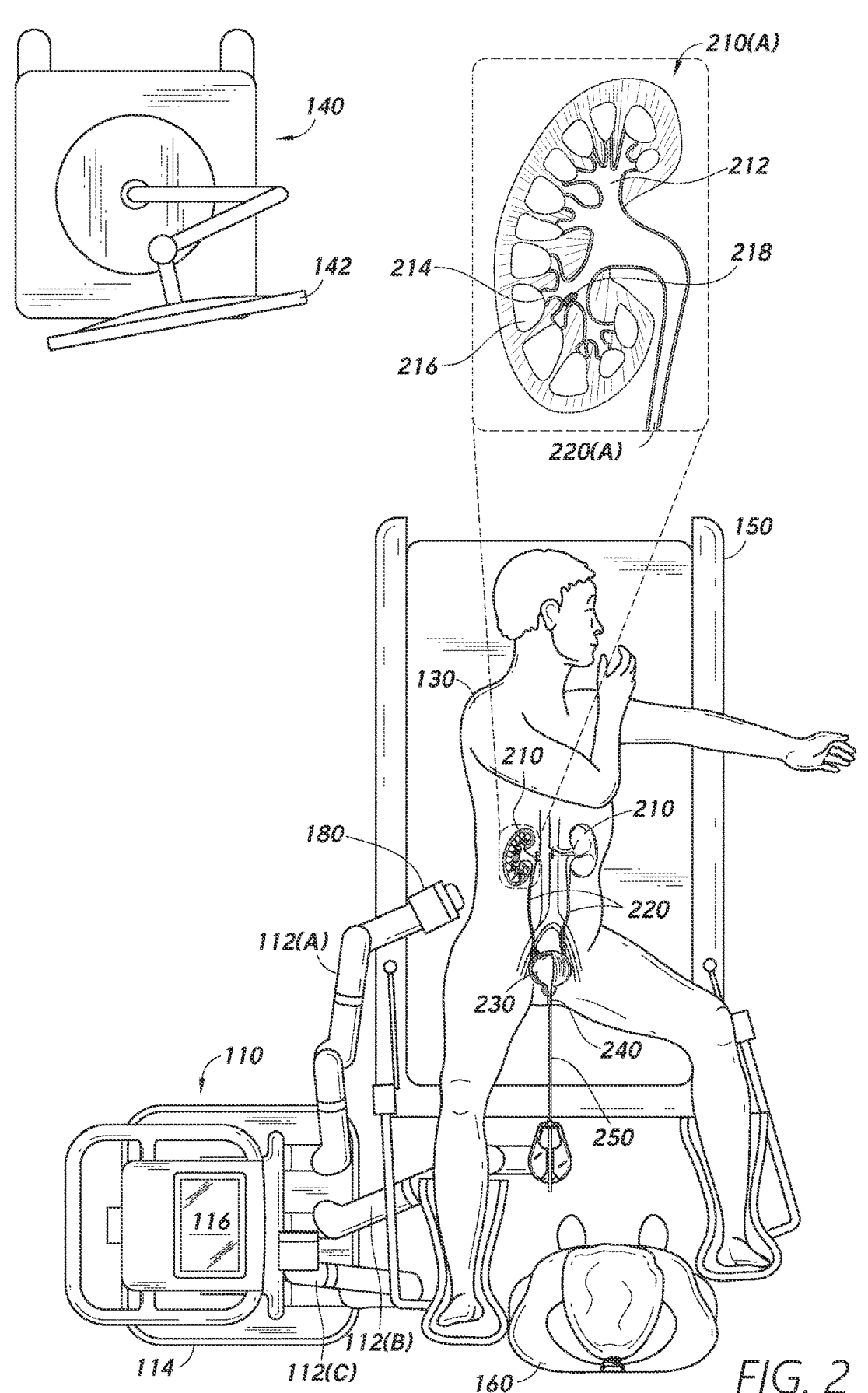
FIG. 2 illustrates a top view of the medical system of FIG. 1 arranged to assist in inserting a scope into a patient in accordance with one or more embodiments.
Figure 3:
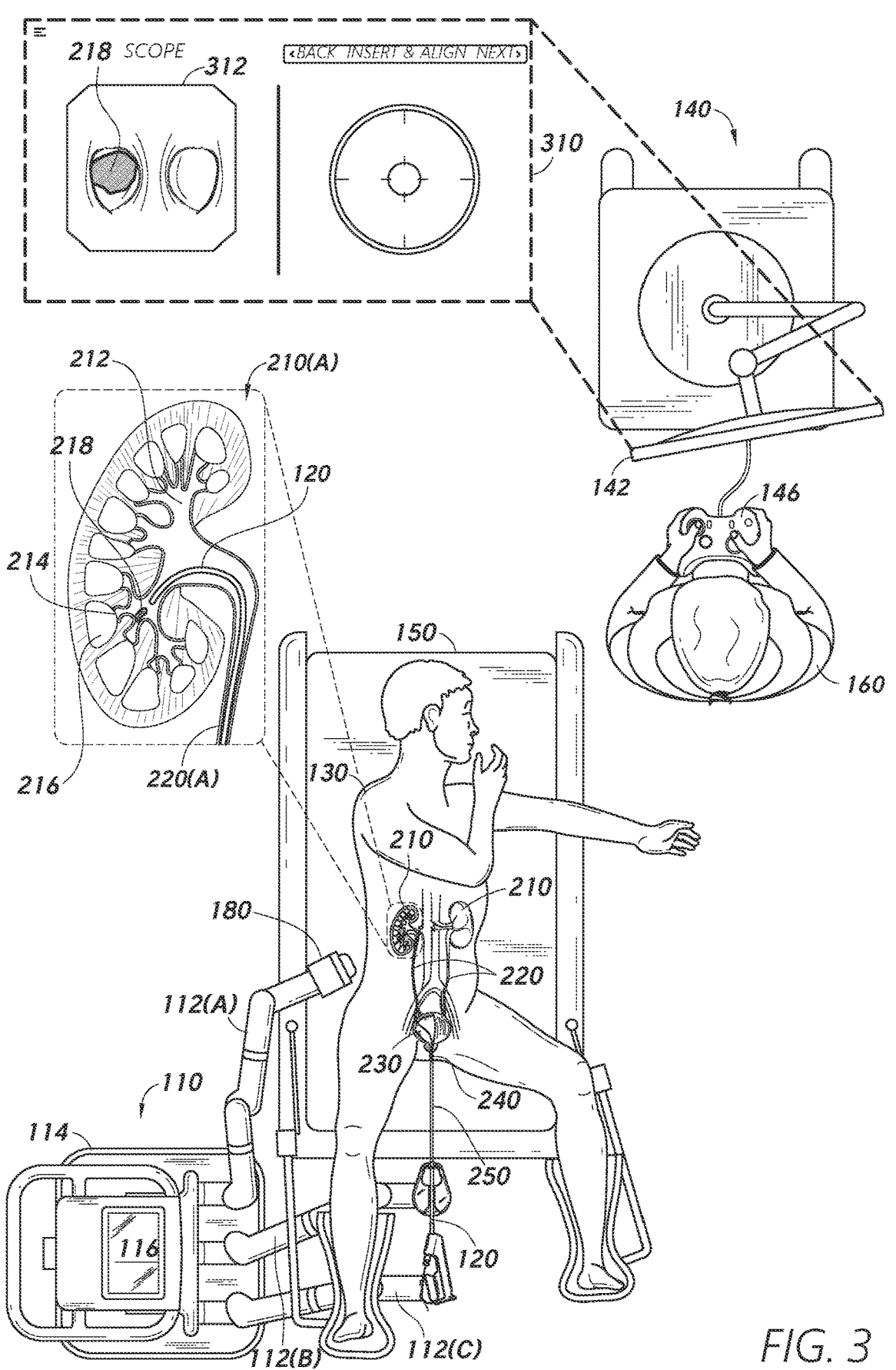
FIG. 3 illustrates a top view of the medical system of FIG. 1 arranged to navigate a scope within a patient in accordance with one or more embodiments.
Figure 4:
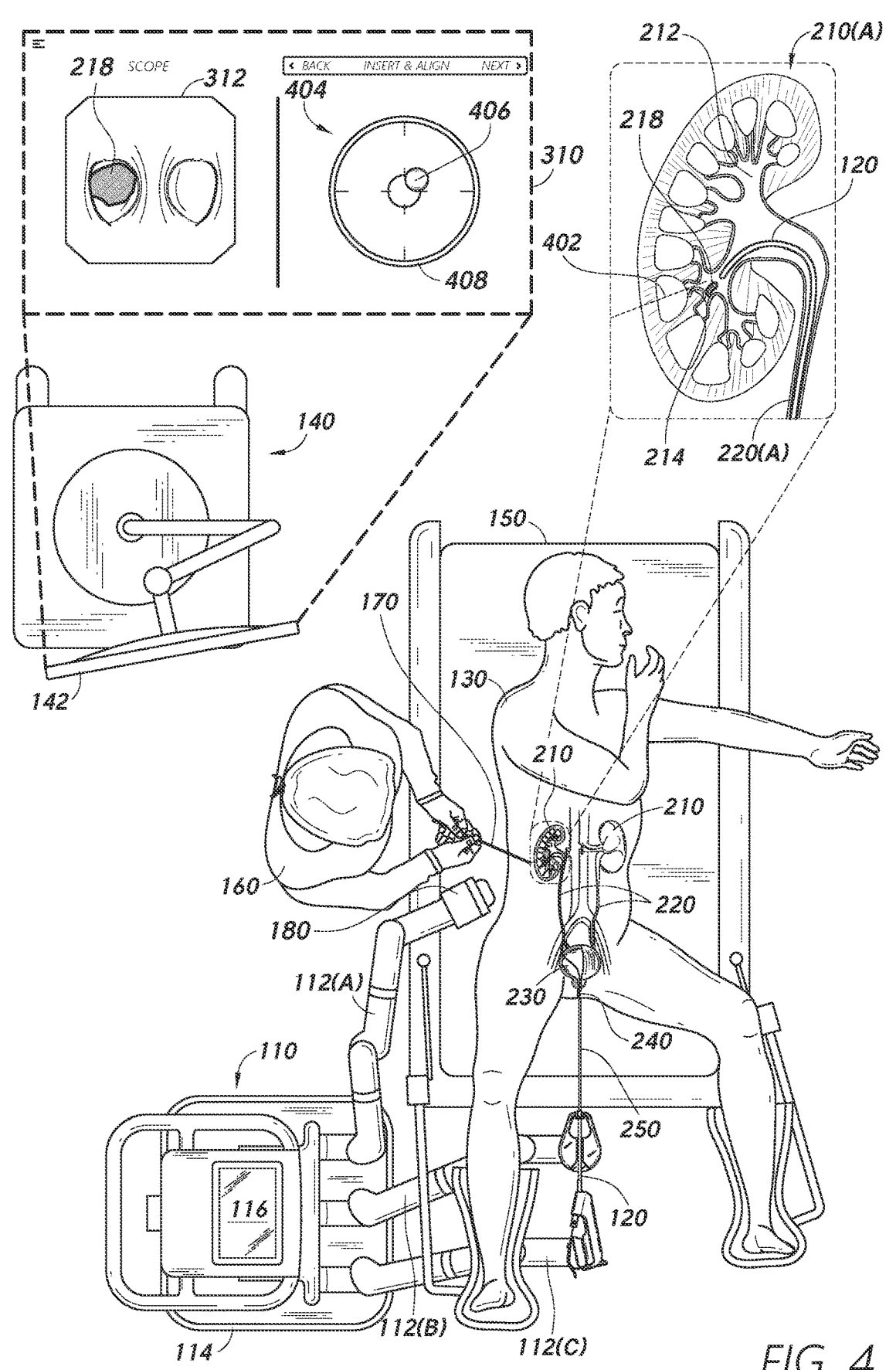
FIG. 4 illustrates a top view of the medical system of FIG. 1 arranged to assist in inserting a needle into a patient in accordance with one or more embodiments.

FIGS. 2-4 illustrate a top view of the medical system 100 of FIG. 1 arranged to perform a percutaneous procedure in accordance with one or more embodiments. In these examples, the medical system 100 is arranged in an operating room to remove a kidney stone from the patient 130 with the assistance of the scope 120 and the needle 170. In many embodiments of such a procedure, the patient 130 is positioned in a modified supine position with the patient 130 slightly tilted to the side to access the flank of the patient 130, such as that illustrated in FIG. 1. However, the patient 130 can be positioned in other manners, such as a supine position, a prone position, and so on. For ease of illustration in viewing the anatomy of the patient 130, FIG. 2-4 illustrate the patient 130 in a supine position with the legs spread apart. Also, for ease of illustration, the imaging device 190 (including the C-arm) has been removed.

Although FIGS. 2-4 illustrate use of the medical system 100 to perform a percutaneous procedure to remove a kidney stone from the patient 130, the medical system 100 can be used to remove a kidney stone in other manners and/or to perform other procedures. Further, the patient 130 can be arranged in other positions as desired for a procedure. Various acts are described in FIGS. 2-4 and throughout this disclosure as being performed by the physician 160. It should be understood that these acts can be performed directly by the physician 160, a user under direction of the physician, another user (e.g., a technician), a combination thereof, and/or any other user.

The renal anatomy, as illustrated at least in part in FIGS. 2-4, is described here for reference with respect to certain medical procedures relating to aspects of the present concepts. The kidneys generally comprise two bean-shaped organs located on the left and right in the retroperitoneal space. In adult humans, the kidneys are generally about 11 cm in length. The kidneys receive blood from the paired renal arteries; blood exits into the paired renal veins. Each kidney is attached to a ureter, which is a tube that carries excreted urine from the kidney to the bladder. The bladder is attached to the urethra.

The kidneys are typically located relatively high in the abdominal cavity and lie in a retroperitoneal position at a slightly oblique angle. The asymmetry within the abdominal cavity, caused by the position of the liver, typically results in the right kidney being slightly lower and smaller than the left, and being placed slightly more to the middle than the left kidney. On top of each kidney is an adrenal gland. The upper parts of the kidneys are partially protected by the 11th and 12th ribs. Each kidney, with its adrenal gland is surrounded by two layers of fat: the perirenal fat present between renal fascia and renal capsule and pararenal fat superior to the renal fascia.

The kidney participates in the control of the volume of various body fluid compartments, fluid osmolality, acid-base balance, various electrolyte concentrations, and removal of toxins. The kidneys provide filtration functionality by secreting certain substances and reabsorbing others. Examples of substances secreted into the urine are hydrogen, ammonium, potassium, and uric acid. In addition, the kidneys also carry out various other functions, such as hormone synthesis, and others.

A recessed area on the concave border of the kidney is the renal hilum, where the renal artery enters the kidney and the renal vein and ureter leave. The kidney is surrounded by tough fibrous tissue, the renal capsule, which is itself surrounded by perirenal fat, renal fascia, and pararenal fat. The anterior (front) surface of these tissues is the peritoneum, while the posterior (rear) surface is the transversalis fascia.

The functional substance, or parenchyma, of the kidney is divided into two major structures: the outer renal cortex and the inner renal medulla. These structures take the shape of a plurality of cone-shaped renal lobes, each containing renal cortex surrounding a portion of medulla called a renal pyramid. Between the renal pyramids are projections of cortex called renal columns. Nephrons, the urine-producing functional structures of the kidney, span the cortex and medulla. The initial filtering portion of a nephron is the renal corpuscle, which is located in the cortex. This is followed by a renal tubule that passes from the cortex deep into the medullary pyramids. Part of the renal cortex, a medullary ray is a collection of renal tubules that drain into a single collecting duct.

The tip, or papilla, of each pyramid empties urine into a respective minor calyx; minor calyces empty into major calyces, and major calyces empty into the renal pelvis, which transitions to the ureter. At the hilum, the ureter and renal vein exit the kidney and the renal artery enters. Hilar fat and lymphatic tissue with lymph nodes surrounds these structures. The hilar fat is contiguous with a fat-filled cavity called the renal sinus. The renal sinus collectively contains the renal pelvis and calyces and separates these structures from the renal medullary tissue.

FIGS. 2-4 show various features of the anatomy of the patient 130. For example, the patient 130 includes kidneys 210 fluidly connected to a bladder 230 via ureters 220, and a urethra 240 fluidly connected to the bladder 230. As shown in the enlarged depiction of the kidney 210(A), the kidney 210(A) includes calyces (including calyx 212), renal papillae (including the renal papilla 214, also referred to as "the papilla 214"), and renal pyramids (including the renal pyramid 216). In these examples, a kidney stone 218 is located in proximity to the papilla 214. However, the kidney stone 218 can be located at other locations within the kidney 210(A) or elsewhere.

As shown in FIG. 2, to remove the kidney stone 218 in the example percutaneous procedure, the physician 160 can position the robotic system 110 at the side/foot of the table 150 to initiate delivery of the scope 120 (not illustrated in FIG. 2) into the patient 130. In particular, the robotic system 110 can be positioned at the side of the table 150 within proximity to the feet of the patient 130 and aligned for direct linear access to the urethra 240 of the patient 130. In examples, the hip of the patient 130 is used as a reference point to position the robotic system 110. Once positioned, one or more of the robotic arms 112, such as the robotic arms 112(B) and 112(C), can stretch outwards to reach in between the legs of the patient 130. For example, the robotic arm 112(B) can be controlled to extend and provide linear access to the urethra 240, as shown in FIG. 2. In this example, the physician 160 inserts a medical instrument 250 at least partially into the urethra 240 along this direct linear access path (sometimes referred to as "a virtual rail"). The medical instrument 250 can include a lumen-type device configured to receive the scope 120, thereby assisting in inserting the scope 120 into the anatomy of the patient 130. By aligning the robotic arm 112(B) to the urethra 240 of the patient 130 and/or using the medical instrument 250, friction and/or forces on the sensitive anatomy in the area can be reduced. Although the medical instrument 250 is illustrated in FIG. 2, in some embodiments, the medical instrument 250 is not used (e.g., the scope 120 can be inserted directly into the urethra 240).

The physician 160 can also position the robotic arm 112(A) near a treatment site for the procedure. For example, the robotic arm 112(A) can be positioned within proximity to the incision site and/or the kidneys 210 of the patient 130. The robotic arm 112(A) can be connected to the EM field generator 180 to assist in tracking a location of the scope 120 and/or the needle 170 during the procedure. Although the robotic arm 112(A) is positioned relatively close to the patient 130, in some embodiments the robotic arm 112(A) is positioned elsewhere and/or the EM field generator 180 is integrated into the table 150 (which can allow the robotic arm 112(A) to be in a docked position). In this example, at this point in the procedure, the robotic arm 112(C) remains in a docked position, as shown in FIG. 2. However, the robotic arm 112(C) can be used in some embodiments to perform any of the functions discussed above of the robotic arms 112(A) and/or 112(C).

Once the robotic system 110 is properly positioned and/or the medical instrument 250 is inserted at least partially into the urethra 240, the scope 120 can be inserted into the patient 130 robotically, manually, or a combination thereof, as shown in FIG. 3. For example, the physician 160 can connect the scope 120 to the robotic arm 112(C) and/or position the scope 120 at least partially within the medical instrument 250 and/or the patient 130. The scope 120 can be connected to the robotic arm 112(C) at any time, such as before the procedure or during the procedure (e.g., after positioning the robotic system 110). The physician 160 can then interact with the control system 140, such as the I/O device(s) 146, to navigate the scope 120 within the patient 130. For example, the physician 160 can provide input via the I/O device(s) 146 to control the robotic arm 112(C) to navigate the scope 120 through the urethra 240, the bladder 230, the ureter 220(A), and up to the kidney 210(A).

As shown, the control system 140 can present an instrument-alignment interface 310, such as the instrument-alignment interface 310 of FIG. 3, via the display(s) 142 to view a real-time image 312 captured by the scope 120 to assist the physician 160 in controlling the scope 120. The physician 160 can navigate the scope 120 to locate the kidney stone 218, as depicted in the image 312. In some embodiment, the control system 140 can use localization techniques to determine a position and/or an orientation of the scope 120, which can be viewed by the physician 160 through the display(s) 142 (not illustrated on the display(s) 142 in FIG. 3) to also assist in controlling the scope 120. Further, in some embodiments, other types of information can be presented through the display(s) 142 to assist the physician 160 in controlling the scope 120, such as x-ray images of the internal anatomy of the patient 130.

Upon locating the kidney stone 218, the physician 160 can identify a location for the needle 170 to enter the kidney 210(A) for eventual extraction of the kidney stone 218. For example, to minimize bleeding and/or avoid hitting a blood vessel or other undesirable anatomy of the kidney 210(A) and/or anatomy surrounding the kidney 210(A), the physician 160 can seek to align the needle 170 with an axis of a calyx (e.g., can seek to reach the calyx head-on through the center of the calyx). To do so, the physician 160 can identify a papilla as a target location. In this example, the physician 160 uses the scope 120 to locate the papilla 214 that is near the kidney stone 218 and designate the papilla 214 as the target location. In some embodiments of designating the papilla 214 as the target location, the physician can cause the medical system to tag the papilla. In tagging the papilla, the physician 160 can navigate the scope 120 to contact the papilla 214 and provide a UI input to the system to indicate the tagging, the control system 140 can use localization techniques to determine a location of the scope 120 (e.g., a location of the end of the scope 120), and the control system 140 can associate the location of the scope 120 with the target location. Additionally or alternatively, the physician 160 can navigate the scope 120 to be within a particular distance to the papilla 214 (e.g., park in front of the papilla 214) and provide input indicating that the target location is within a field-of-view of the scope 120. The control system 140 can perform image analysis and/or other localization techniques to determine a location of the target location. In yet other embodiments, the scope 120 can deliver a fiduciary to mark the papilla 214 as the target location.

As shown in FIG. 4, the physician 160 can proceed with the procedure by positioning the needle 170 for insertion into the target location. In some embodiments, the physician 160 can use his or her best judgment to place the needle 170 on the patient 130 at an incision site, such as based on knowledge regarding the anatomy of the patient 130, experience from previously performing the procedure, an analysis of CT/x-ray images or other pre-operative information of the patient 130, and so on. Further, in some embodiments, the control system 140 can provide information regarding a location to place the needle 170 on the patient 130. The physician 160 can attempt to avoid critical anatomy of the patient 130, such as the colon, paraspinal muscles, ribs, intercostal nerves, lungs, pleura, etc. In some examples, the control system 140 can use CT/x-ray/ultrasound images to provide information regarding a location to place the needle 170 on the patient 130.

In any event, the control system 140 can determine a target trajectory 402 for inserting the needle 170 to assist the physician 160 in reaching the target location (i.e., the papilla 214). The target trajectory 402 can represent a desired path for accessing the target location. The target trajectory 402 can be determined based on a position of a medical instrument (e.g., the needle 170, the scope 120, etc.), a target location within the human anatomy, a position and/or orientation of a patient, the anatomy of the patient (e.g., the location of organs within the patient relative to the target location), and so on. In this example, the target trajectory 402 includes a straight line that passes through the papilla

214 and the needle 170 (e.g., extends from a tip of the needle 170 through the papilla 214, such as a point on an axis of the papilla 214). However, the target trajectory 402 can take other forms, such as a curved line, and/or can be defined in other manners. In some examples, the needle 170 is implemented a flexible bevel-tip needle that is configured to curve as the needle 170 is inserted in a straight manner. Such needle can be used to steer around particular anatomy, such as the ribs or other anatomy. Here, the control system 140 can provide information to guide a user, such as to compensate for deviation in the needle trajectory or to maintain the user on the target trajectory.

Although the example of FIG. 4 illustrates the target trajectory 402 extending coaxially through the papilla 214, the target trajectory 402 can have another position, angle, and/or form. For example, a target trajectory can be implemented with a lower pole access point, such as through a papilla located below the kidney stone 218 shown in FIG. 4, with a non-coaxial angle through the papilla, which can be used to avoid the hip.

The control system 140 can use the target trajectory 402 to provide an alignment-progress visualization 404 via the instrument-alignment interface 310. For example, the alignment-progress visualization 404 can include an instrument alignment element 406 indicative of an orientation of the needle 170 relative to the target trajectory 402. The physician 160 can view the alignment-progress visualization 404 and orient the needle 170 to the appropriate orientation (i.e., the target trajectory 402). When aligned, the physician 160 can insert the needle 170 into the patient 130 to reach the target location. The alignment-progress visualization 404 can provide a progress visualization 408 (also referred to as "the progress bar 408") indicative of a proximity of the needle 170 to the target location. As such, the instrument-alignment interface 310 can assist the physician 160 in aligning and/or inserting the needle 170 to reach the target location.

Once the target location has been reached with the needle 170, the physician 160 can insert another medical instrument, such as a power catheter, vacuum, nephroscope, etc., into the path created by the needle 170 and/or over the needle 170. The physician 160 can use the other medical instrument and/or the scope 120 to fragment and remove pieces of the kidney stone 218 from the kidney 210(A).

In some embodiments, a position of a medical instrument can be represented with a point/point set and/or an orientation of the medical instrument can be represented as an angle/offset relative to an axis/plane. For example, a position of a medical instrument can be represented with a coordinate(s) of a point/point set within a coordinate system (e.g., one or more X, Y, Z coordinates) and/or an orientation of the medical instrument can be represented with an angle relative to an axis/plane for the coordinate system (e.g., angle with respect to the X-axis/plane, Y-axis/plane, and/or Z-axis/plane). Here, a change in orientation of the medical instrument can correspond to a change in an angle of the medical instrument relative to the axis/plane. Further, in some embodiments, an orientation of a medical instrument is represented with yaw, pitch, and/or roll information. In other embodiments, an orientation of a medical instrument is represented in quaternion representation. It is to be appreciated that quaternion representation may avoid singularities present in a representation based on yaw, pitch, and roll.

In some embodiments, a trajectory refers as a pose. For example, a trajectory of a medical instrument can refer to a pose of the medical instrument, including/indicating both a position and orientation of the medical instrument. Similarly, a target trajectory can refer to a target pose, including/indicating both a position and orientation of a desired path. However, in other embodiments, a trajectory refers to either an orientation or a position.

Although particular robotic arms of the robotic system 110 are illustrated (and/or described herein) as performing particular functions in the context of FIGS. 2-4, any of the robotic arms 112 can be used to perform the functions. Further, any additional robotic arms and/or systems can be used to perform the procedure. Moreover, the robotic system 110 can be used to perform other parts of the procedure. For example, the robotic system 110 can be controlled to align and/or insert the needle into the patient 130. To illustrate, one of the robotic arms 112 can engage with and/or control the needle 170 to position the needle 170 at the appropriate location, align the needle 170 with the target trajectory, and/or insert the needle 170 to the target location. The control system 140 can use localization techniques to perform such processing. As such, in some embodiments, a percutaneous procedure can be performed entirely or partially with the medical system 100 (e.g., with or without the assistance of the physician 160).

As demonstrated in the above description relative to FIGS. 2-4, a percutaneous medical procedure may have a number of phases. To simplify the discussion of embodiments contemplated by this disclosure, four example phases are now provided. However, it should be appreciated that other embodiments can have more, less, or even different phases and the following phases are provided merely as an illustration and not a limitation.

Target selection: This phase can include the activities performed to set a target inside the kidney. For example, as described above, a ureteroscope can be driven to a target calyx, tag a papilla, parked at a distance away from the papilla, and "Set" to set a live target.

Site selection: This phase can include the activities from when the user selects a target to the moment when the user positions the needle tip at a specific location on the patient's skin with the intention to puncture the skin towards the kidney.

Needle Insertion: This phase includes time periods during which a user inserts the needle into the patient and stops with no intention to push the needle further. During needle insertion, a user can puncture the skin and insert the needle from the skin towards the target. This attempt may be referred to as a first needle insertion. If the user misses the target, a medical system may instruct the user to retract the needle (in some embodiments, while keeping the needle inside the body) and attempt another needle insertion (e.g., a secondary needle insertion). Even though there is a distinction between first needle insertion and the secondary insertion attempts, some embodiments may treat them as the same while other embodiments may treat them as different attempts.

Post Insertion: This phase encompasses the activities between consecutive/sequential needle insertion phases, if such exist, and the duration from the last needle insertion until the end of the percutaneous procedure.

Example Segmentation

Figure 5:
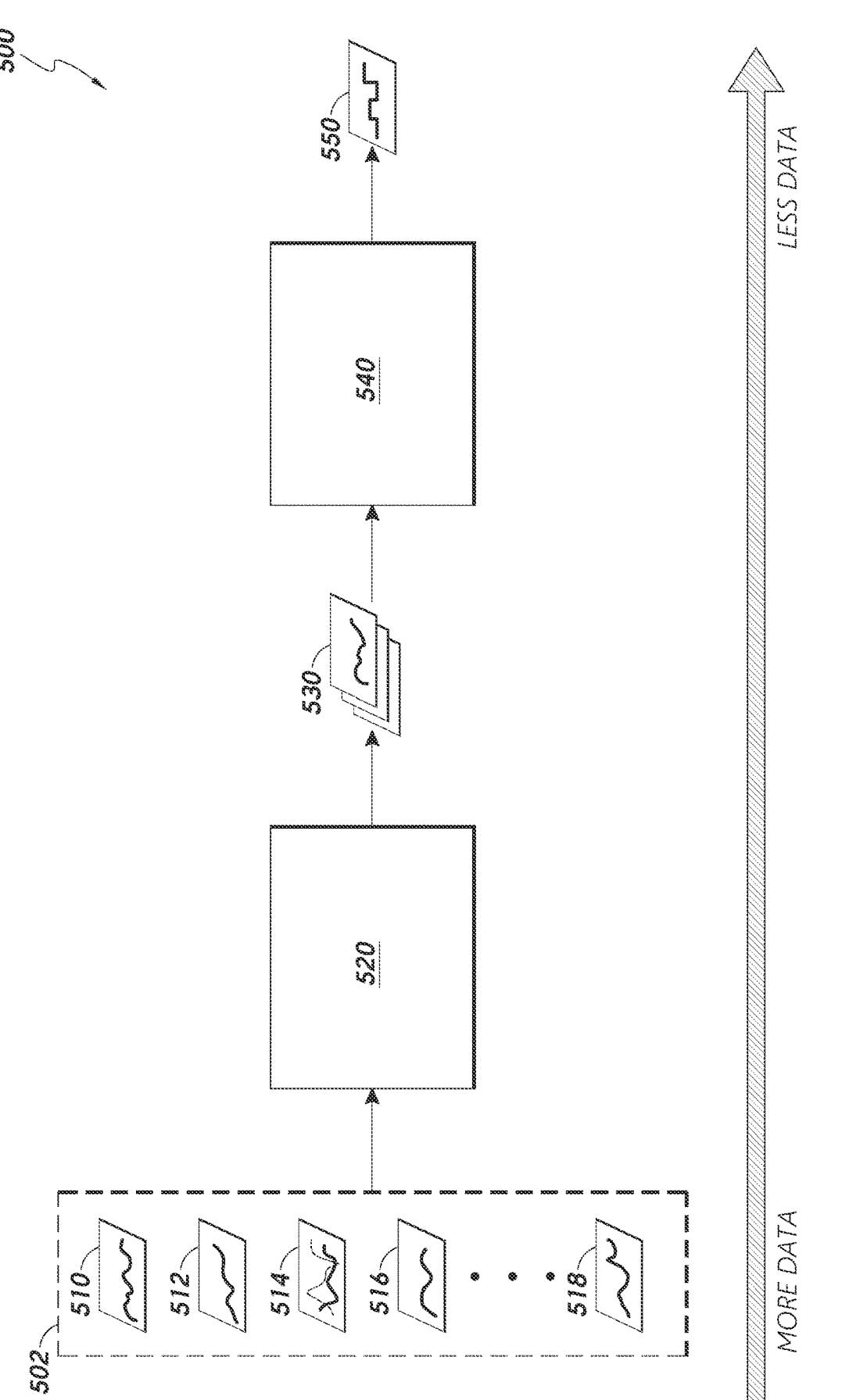
FIG. 5 is a block diagram illustrating an analytics engine configured to implement the techniques discussed herein in accordance with one or more embodiments.

FIG. 5 is a block diagram illustrating an analytics engine 500 configured to implement the techniques discussed herein in accordance with one or more embodiments. As discussed above, the analytics engine 500 may receive and process the case logs 502 intraoperatively or postoperatively. In embodiments that receive and process the case logs intraoperatively, the analytics engine 500 may be a component of a control system of a medical system, such as the analytics engine 141A of the control system 140 shown in FIG. 1. In embodiments that receive and process the case logs postoperatively, the analytics engine 500 may be a component of a cloud-based data analytics platform connected to a medical system (or medical systems), such as the analytics engine 141B of the cloud-based data analytics platform 149 shown in FIG. 1.

As FIG. 5 shows, the analytics engine 500 may receive case logs 502. As previously discussed, case logs may include runtime data a medical system collects and otherwise stores during the operation of the medical system as a medical procedure is performed. As FIG. 5 shows, the case logs 502 may include robotic telemetry data 510, instrument telemetry data 512, video data 514, device status data 516, and I/O data 518. The robotic telemetry data 510 may be time series data that represents the various poses, movements, and actuations of the robotic system, including the robotic arm joints and actuators. It is to be appreciated that such poses, movements, actuations of the robotic system may be part of a kinematics model of the system that can estimate not only the pose of the robotic arms but also, with known properties of the instrument, the pose of the instrument attached and otherwise controlled by the robotic system, such as a robotically controlled endoscope.

The instrument telemetry data 512 includes time series data that represents the positioning of the instruments based on sensor data. For example, as discussed above, a percutaneous needle may include an EM sensor that allows the system to record and determine the needle's location within an EM space. The system may record this EM space data to track the needle's location over time. It is to be appreciated that the instrument telemetry data 512 may include sensor data other than EM data, such as shape sensing fiber, accelerometers, a gyroscope, a satellite-based positioning sensor (e.g., a global positioning system (GPS)), a radio-frequency transceiver, and so on, embedded on a medical instrument.

The instrument telemetry data 512 may also include time series data that represents the positioning of the scope. For example, as discussed above, a scope instrument may include an EM sensor that allows the system to record and determine the scope instrument's location within an EM space. The system may record this EM space data to track the scope instrument's location over time. It is to be appreciated that the instrument telemetry data 512 may include sensor data other than EM data, such as shape sensing fiber, accelerometers, a gyroscope, a satellite-based positioning sensor (e.g., a global positioning system (GPS)), a radio-frequency transceiver, and so on, embedded on a medical instrument.

The video data 514 may be data that represents the live video data captured by the camera on the end of the endoscope instrument. In some embodiments, the operating room and/or the robotic system may be equipped with imaging devices external to the patient and the video data 514 may include this type of video data as well.

The device status data 516 may include time series data that represent, among other things, statuses of components of the medical system, statuses of the instruments connected to the medical system, the user interface menu page shown to the users by the medical system, and any other suitable device status. As an example, the medical system 100 may include radio-frequency identification ("RFID") readers capable of reading RFID tags on medical instruments attached to the robotic system. The device status data 516 may include indicators associated with the medical instruments, as obtained by those RFID tags. Still further, in some embodiments, where the medical instruments include EM sensors, the device status data 516 may include data indicative of whether the medical instrument is connected to the EM system and whether the medical instrument is within an EM field of an EM field generator of the EM system. The device status data 516 may further include a state of the robot. For example, the robot could be in scope driving state, basketing state, lasering state, and the like. This robot state is derived from instrument connection status and what UI page is being displayed to the user (which may, for example, be identified in the data of the I/O data 518).

The I/O data 518 may include time series data that represent, among other things, the commands transmitted by the I/O devices of the medical system. For example, the I/O data 518 may include data representing instrument drive commands (e.g., insert/retract) or articulation commands (e.g., articulate left, articulate right, articulate up, articulate down, roll scope). In some embodiments, the I/O data 518 may include additional I/O commands that may represent events in the percutaneous procedures, like tag a papilla and parking the scope. These events may be determined based on the UI page currently being displayed by the medical device system. The I/O data 518 may, additionally or alternatively, include data representing the user's interactions with the UI displayed by the percutaneous access interface 144.

It is to be appreciated that, as used herein, timeseries data may include measurements or events that are tracked, monitored, down sampled, or aggregated over time. In some cases, the timeseries data described above may be a stream of data from a sensor according to some determinable frequency (e.g., based on sample rate of a sensor or event logger). In those cases, time may be derived based on some known time and the position of the sensor data in the stream. In other cases, the timeseries data may include events generated from the system. In those cases, the events may include a timestamp (or a range of timestamps) that identifies the time in which the event occurred and possible duration. In some embodiments, the duration of an event may be inferred based on the occurrence of the next timestamp event. In other cases, events may be represented as a stream of events currently triggered in the stream, and timing may be inferred from a known time and the position of the event in the stream of events.

FIG. 5 shows that a feature extractor module 520 receives the case logs 502. The feature extractor module 520 is a module that analyzes the case logs 502 and outputs a set of one or more case log features 530. Different exemplary case log features are discussed in greater detail below, but case log features can include features related to the scope position in a world frame (e.g., the coordinate frame of the robotic system), the needle position in a world frame, target position in the world frame, distances between components (e.g., needle, scope, target, etc.), orientation between components (e.g., needle, scope, target, etc.), and the like.

A phase segmentation module 540 receives the case log features 530 and generates a times series class prediction for whether the medical procedure is within a determinable phase, shown as segmented procedure data 550. In the case of percutaneous access, the phase segmentation module 540 may output a binary classification where class A represents 'Needle Insertion Phase' and class B represents 'Other Phase'. In other embodiments, the phase segmentation module 540 may output a multi-class classification where class A represents 'Needle Insertion Phase', class B represents 'Target Selection Phase', class C represents 'Site Selection Phase', and class D represents 'Post-Needle Insertion Phase'. It is to be appreciated that these classifications are merely examples and some embodiments may have more, less, or different classifications depending on the medical procedure.

The phase segmentation module 540 may estimate a phase of the medical procedure based on any suitable machine learning method, including but not limited to, hidden Markov models (HMM), long-term-short-memory networks, and deep-learning based methods, such as convoluted neural networks ("CNNs" or "CNN" in the singular). In some cases, additionally or alternatively, an engineered approach to phase estimating may be used with the machine learning methods. For example, an engineered approach may use conditional logic to determine whether the medical procedure is in a 'Needle Insertion Phase'. This is described in greater detail below.

As FIG. 5 shows, the data processed by the system may reduce in terms of data size as data moves from left to right. For example, the case logs 502 are comparatively larger in data volume than the extracted feature data of the case log features 530 because the feature extractor module 520 narrows down the data from the case logs into the features that are impactful for phase segmentation. To accomplish this, the feature extractor module may combine multiple data values from the case logs to produce one value or may selectively filter out data that is not useful in the segmentation algorithms. Further reducing the data size, the extracted feature data of the case log features 530 is comparatively larger in data volume than the segmented procedure data 550, as the segmented procedure data 550 reduces the potentially many features over time into a classification over time. By reducing the dataset, and making sure the data is relevant and suited to the segmentation algorithms, the systems and methods described herein offer a segmentation solution that is highly computationally efficient. Further, while this disclosure is largely directed to percutaneous medical procedures, it has greater clinical utility and can be adapted to a variety of procedures. Accordingly, data can be filtered with respect to a respective medical procedure of interest, and one can avoid the computational overhead involved in looking at the entire data universe of the medical procedure.

Example Case Log Features

As discussed above with reference to FIG. 5, the phase segmentation module 540 may receive a number of case log features to segment the medical procedure based on phases. By way of example and not limitation, exemplary case log features that a phase segmentation module may receive include:

Needle Position: Time series data that defines the three-dimensional needle position (e.g., needle 170) in a world frame over time. As used herein, the world frame may refer to a frame of reference defined by a coordinate system that is not tied to the patient's body. Such a world frame may be defined by an EM field generator if such a system of needle tracking is used. If, additionally or alternatively, shape sensing fiber is used for tracking the position of the needle, then the world frame would be defined by the coordinate system used in that system, typically from a known position. Accordingly, the medical system 100 may repeatedly record the current position of the needle in the case logs based on sensor data received from a positional sensor attached to the needle instrument 170.

Needle Orientation: Time series data that defines the orientation of the needle 170, such may be represented or otherwise measured in Euler angles or quaternion.

Similar to the needle position, this feature may be measured relative to a world frame. Likewise, the medical system 100 may repeatedly record the current orientation of the needle in the case logs based on sensor data generated by a positional sensor attached to the needle instrument 170 and use those sensor data to generate this feature.

Scope Position: Time series data that defines the three-dimensional position of the scope 120 in a world frame. As discussed above, the scope may include an EM sensor and, in such embodiments, the medical system 100 may repeatedly record the current reading of the EM sensor corresponding to the scope 120 in the case logs. Additionally or alternatively, in embodiments where the scope 120 includes other types of location sensors, the current reading from those location sensors (e.g., shape sensing fiber, accelerometer, gyroscope, and the like) may be recorded and used to generated this feature.

Scope Orientation: Time series data that defines the orientation measurements of the scope 120, such may be measured or otherwise expressed in as Euler angles or a quaternion. This feature may be measured relative to a world frame and may be derived from a location sensor on the scope 120, such as an EM sensor or a shape sensing fiber.

Target Position: Time series data that defines the three-dimensional target position in a world frame. As discussed above, the target position may be a user-initiated location established by the medical system during the target selection phase. For example, the medical system 100 may set the target position in three-dimensional EM space responsive to receiving a 'Set' command from the user, as may occur after a user tags a papilla and parks a scope some distance away from the papilla. Because the 'target position' feature involves a user command and a position of the scope at the time the user command was received, embodiments may generate a target position responsive to a position of the scope (as may be determined from the sensor data received from the scope) at the time that an I/O event was received indicating that a user has set a target.

Target Orientation: Time series data that defines the orientation measurements of a target, such may be measured or otherwise expressed in Euler angles or a quaternion. This feature may be measured relative to a world frame and, as discussed above, may be derived from a user-initiated position recorded during the target selection phase. Further, a 'target orientation' feature may be derived similar to a 'target position' feature in that embodiments may generate a target orientation responsive to an orientation of the scope (as may be determined from the sensor data received from the scope) at the time that an I/O event was received indicating that a user has set a target.

Needle Alignment Error: Time series data that represents the distance between the target and a representation of alignment generated to assist a user performing a percutaneous medical procedure. In some embodiments, this distance is also displayed via instrument alignment element 406 of FIG. 4 as a representation on a physical plane with a 'bullseye' or target position.

Relative Needle Scope Heading: Time series data representing a comparison of the angles between a needle 170 and a scope 120. This feature may be derived based on determining an angle between a vector representing the orientation of the needle and a vector representing the orientation of the scope.

Distance to Target: Time series data representing a measurement of a distance between the needle 170 and the target. In some embodiments, this feature may be derived based on a distance between the position of a needle and a target.

Distance to Target Plane: Time series data representing a measurement of the distance from a position of the needle 170 to a plane or point representing a target location or a plane through the target.

Relative Needle Scope $3d$ Distance: Time series data representing a measurement of the location of a scope 120 relative to a coordinate frame of a needle.

Alignment Error: Time series data representing an angular deviation from a vector connecting a scope 120 and needle 170 to a current vector of the needle.

Scope Linear Body Velocity: Time series data representing the linear body velocity of a scope 120, as may be measured by, or otherwise derived from data sensed by, a positional sensor in the scope.

Scope Angular Body Velocity: Time series data representing the angular body velocity of a scope 120, as may be measured by, or otherwise derived from data sensed by, a positional sensor in the scope.

Scope Absolute Speed: Time series data representing the absolute body speed of a scope 120, as may be measured by, or otherwise derived from data sensed by, a positional sensor in the scope. In some embodiments, the scope absolute speed feature may be a norm of the scope linear body velocity.

Needle Linear Body Velocity: Time series data representing the linear body velocity of the needle 170, as may be measured by, or otherwise derived from data sensed by, a positional sensor in the needle.

Needle Angular Body Velocity: Time series data representing the angular body velocity of the needle 170, as may be measured by, or otherwise derived from data sensed by, a positional sensor in the needle.

Needle Absolute Speed: Time series data representing the absolute body speed of the needle 170, as may be measured by or otherwise derived from data sensed by a positional sensor in the needle 170. In some embodiments, the needle absolute speed feature may be the norm of the needle linear body velocity.

Example Classification

Figure 6A:
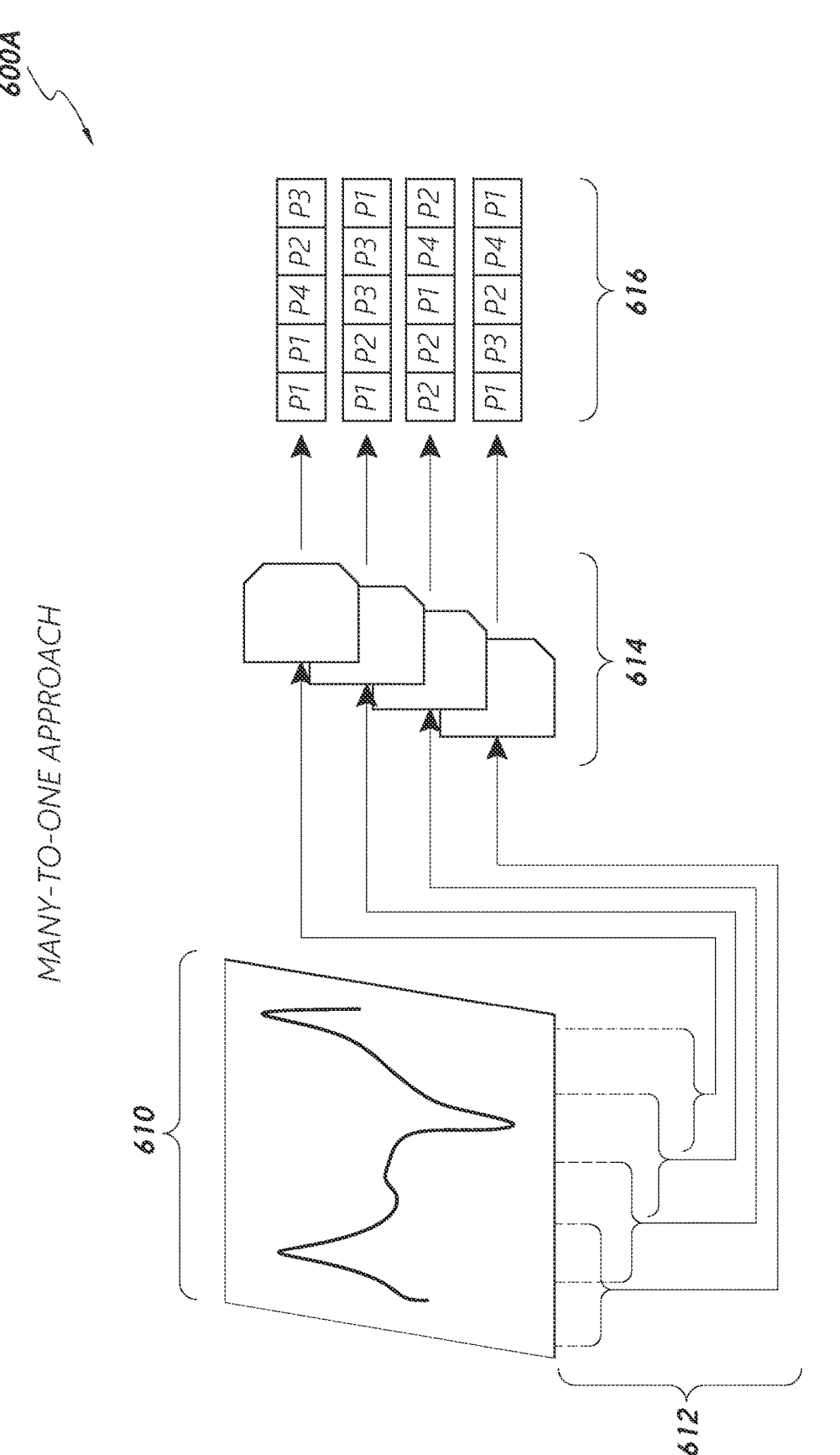
FIG. 6A is a block diagram illustrating a many-to-one phase segmentation module for classifying the time series data derived from the case logs in accordance with one or more embodiments.

As discussed above, some embodiments may segment a medical procedure according to procedure phases using data (e.g., features) derived from case logs. Segmentation in this context may be solved as a classification problem where the time series data (e.g., data derived from the case logs) are classified with corresponding medical procedure phases to which the time series data belongs. Various aspects of classification are now discussed with reference to FIGS. 6A-D. FIG. 6A is a block diagram illustrating a many-to-one phase segmentation module 600A for classifying the time series data derived from the case logs, as may be implemented in the phase segmentation module 540 shown in FIG. 5.

As FIG. 6A shows, the many-to-one phase segmentation module 600A may receive input time series 610. The input time series 610 may be case log features. Case log features are discussed in greater detail with reference to FIG. 5, but, without limitation, may include data derived from robotic telemetry data, instrument telemetry data, video data, device status data, I/O data, and the like. As shown in FIG. 6A, the many-to-one phase segmentation module 600A may divide the input time series 610 data into windowed segments 612, which are then input to the model evaluation block 614. In the model evaluation block 614, there are one or a plurality of model evaluations, one for each windowed segment. Each model evaluation then generates output predictions for the corresponding phase segments.

It is to be appreciated that the many-to-one phase segmentation module 600A can provide phase segmentation for comparatively smaller window feature segments and may not necessarily require a complete set of data characterizing the medical procedure. As such, a many-to-one phase segmentation approach, as shown in FIG. 6A, may be used for real-time or near real-time phase detection (e.g., intraoperative phase detection). Further, it is to be appreciated that given the intraoperative applicability, a local analytics engine (e.g., the local analytics engine 141A in FIG. 1) may utilize a many-to-one segmentation module similar to the many-to-one phase segmentation module 600A shown in FIG. 6A.

It is to be appreciated that in some embodiments, a many-to-one phase segmentation may be near real-time but not real-time because such an approach is delayed by the window feature segment. One approach that can be used by other embodiments to make many-to-one phase segmentation approaches real-time is to use a time series prediction module. Time series prediction takes in a window feature segment and predicts the next window feature segment. A time series prediction module can include a time series prediction network trained to predict the next window feature segment. During execution of the many-to-one phase segmentation, features would feed into a time series prediction network to predict the next window of features. The output of the time series prediction network would then feed into the time series classification of the many-to-one phase segmentation to predict the phase of the procedure for that window feature segment.

Figure 6B:
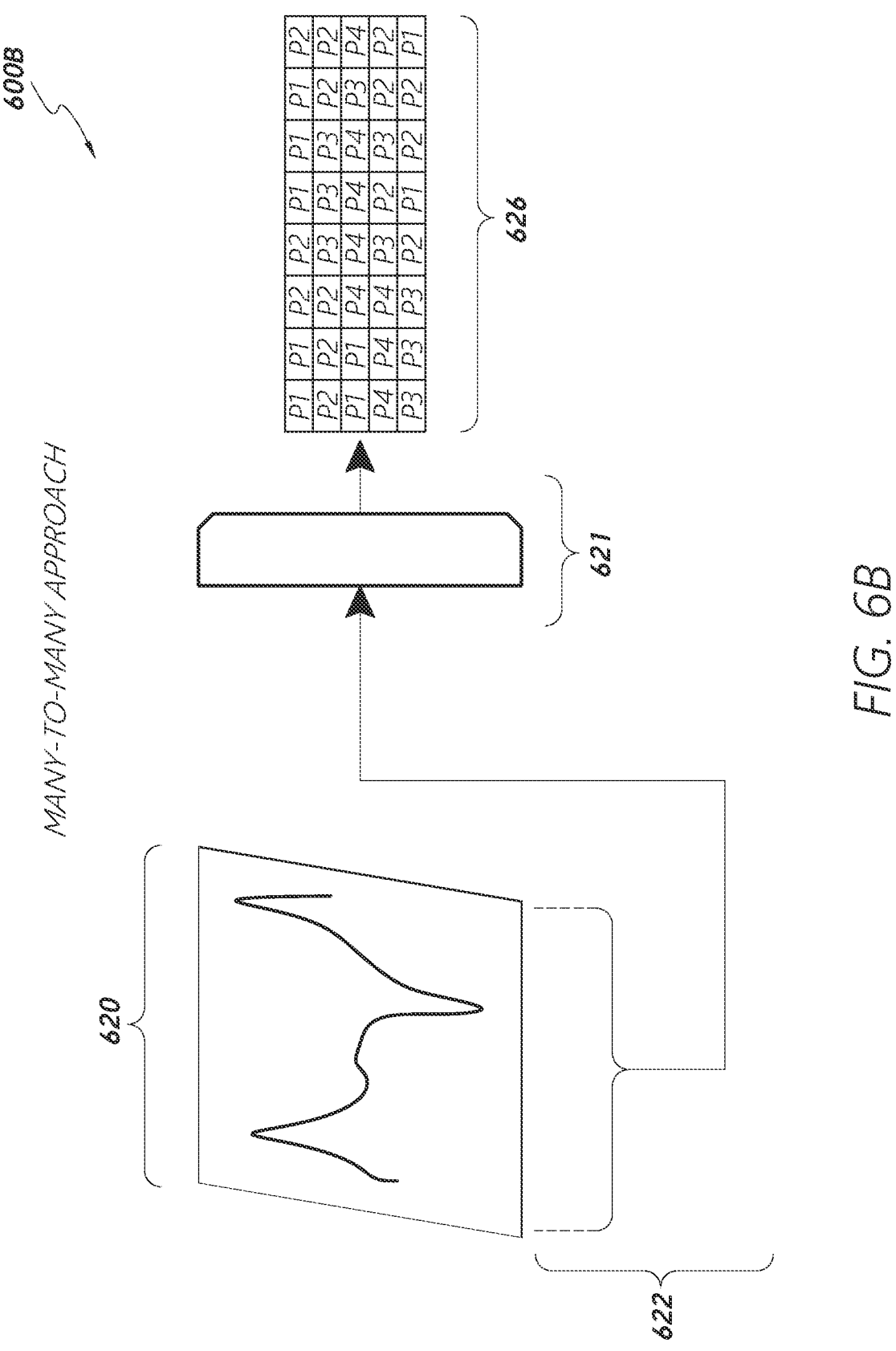
FIG. 6B is a block diagram illustrating a many-to-many phase segmentation module for classifying the time series data in the case logs in accordance with one or more embodiments.

FIG. 6B is a block diagram illustrating a many-to-many phase segmentation module 600B for classifying the time series data in the case logs, as may be implemented in the phase segmentation module 540 described in reference to FIG. 5.

As FIG. 6B shows, the many-to-many phase segmentation module 600B may receive time series data 620. The time series data 620 may be features derived from case logs. Case log features are discussed in greater detail above with reference to FIG. 5 but may include, without limitation, data derived from robotic telemetry data, instrument telemetry data, video data, device status data, and I/O data, and the like. As shown in FIG. 6B, the many-to-many phase segmentation module 600B may divide the input timeseries 620 into comparatively longer windowed feature segments 622 with respect to the many-to-one phase segmentation module 600A shown in FIG. 6A, which are then input to the model evaluation block 621. In the model evaluation block 621, there are few (or comparatively fewer) model evaluations, and many (or comparatively more) output predictions 626 for the corresponding feature segments.

It is to be appreciated that the many-to-many phase segmentation module 600B may operate with a single model evaluation and can be applied to time series data of arbitrary length. As such, the many-to-many phase segmentation module 600B may be useful for post-operative analytics given that many-to-many phase segmentation module 600B may be more robust compared to the many-to-one phase segmentation module 600A. When used post-operatively, the training set used by the many-to-many phase segmentation module 600B may include data obtained from multiple prior procedures, potentially via multiple medical systems, and this training set may be built up over time. To illustrate with temporary reference to FIG. 1, the cloud-based data analytics platform 149 may utilize a many-to-many segmentation module similar to the many-to-many phase segmentation module 600B shown in FIG. 6B. The model evaluation used by the cloud-based data analytics platform 149 may be trained using data obtained from (or derived from data obtained from) the additional medical systems 103.

FIG. 6C is a diagram showing a binary classification approach that a segmentation module (e.g., many-to-one phase segmentation module 600A or many-to-many phase segmentation module 600B) may incorporate. As shown, based on the time series data derived from the case log features, a segmentation module may generate medical procedure phase classifications in the form of a time series labels. The medical procedure phase classifications may be binary classifications that identify whether the predicted phase is the Needle Insertion phase (e.g., classifications 660A and 660B) or not (e.g., classifications 680A, 680B, 680C). In some embodiments, the segmentation module may then execute higher-level decision processing to uncover the other classifications within the not 'Needle Insertion' phase (e.g., classifications 680A, 680B, 680C). This approach may be useful in a fully convolutional neural network, such as U-Net.

Figure 6D:
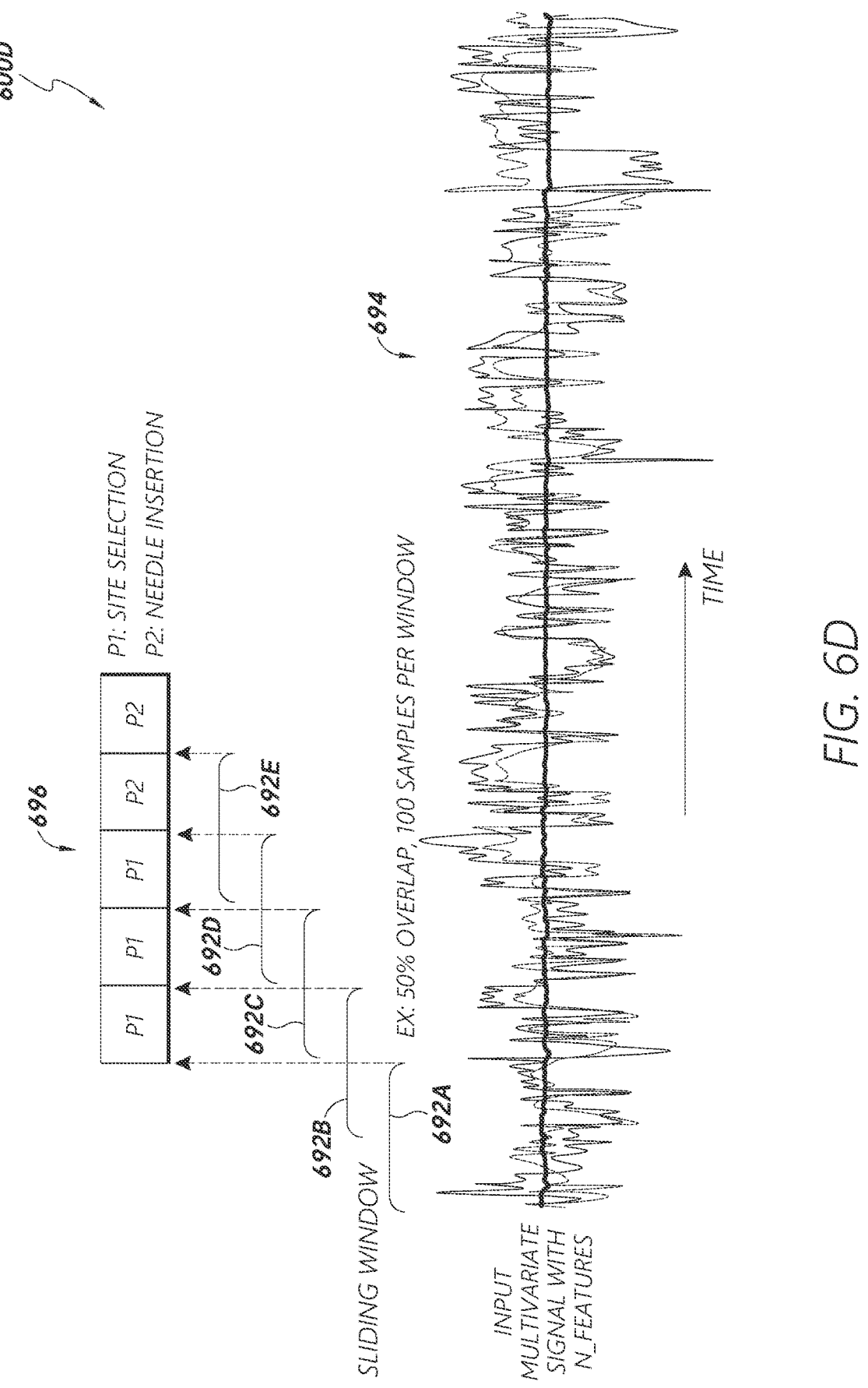
FIG. 6D is a diagram showing the output of a segmentation module with multiple classification of labels in accordance with one or more embodiments.

Rather than using binary classification, some embodiments of a segmentation module (e.g., many-to-one phase segmentation module 600A or many-to-many phase segmentation module 600B) may use a multi-class classification architecture. For example, rather than merely classifying the medical procedure phase as Needle Insertion or Not, embodiments may further classify the time series data to further include one or more of: Target Selection, Site Selection, Post Needle Insertion, and the like. FIG. 6D is a diagram showing the output 600D of a segmentation module with multiple classification. Further the output 600D is shown in the context of a many-to-many classification, where there are sliding segmentation windows 692A-E. Here, each of the sliding segmentation windows 692A-E correspond to different time periods in the segmentation features 694. Further, a sliding segmentation window may overlap in time with neighboring sliding segmentation windows. For example, sliding segmentation window 692B may correspond to a time period that overlaps the time period associated with sliding segmentation window 692A and a time period that overlaps with the time period associated with sliding segmentation window 692C. In some cases, there is a 50% overlap but this overlap may be different depending on the application and the size of the data sets used to train the models. For example, other overlaps may include overlaps of 25% or less given enough training data. It is to be appreciated that the window lengths are also application specific, and this disclosure does not limit itself to any particular window length. In the context of percutaneous medical procedures, this disclosure has identified window lengths of 3-10 seconds as being useful in those procedures.

The sliding segmentation windows 692A-E are then used (e.g., by one or more evaluations of model evaluation block 614) to generate the medical procedure phase classifications 616.

FIG. 6D may represent an approach used by a parallel CNN long short-term memory ("LSTM"). A Parallel CNN-LSTM may use CNN layers and an attention LSTM layer in parallel. This contrasts with common serial CNN LSTM architectures, where CNNs are used to encode features and the LSTM layer is used to model long-term dependencies of the features across time. A Parallel CNN-LSTM can be used in a many-to-one architecture, as described with reference to FIG. 6A.

Example Segmentation Method

Figure 7:
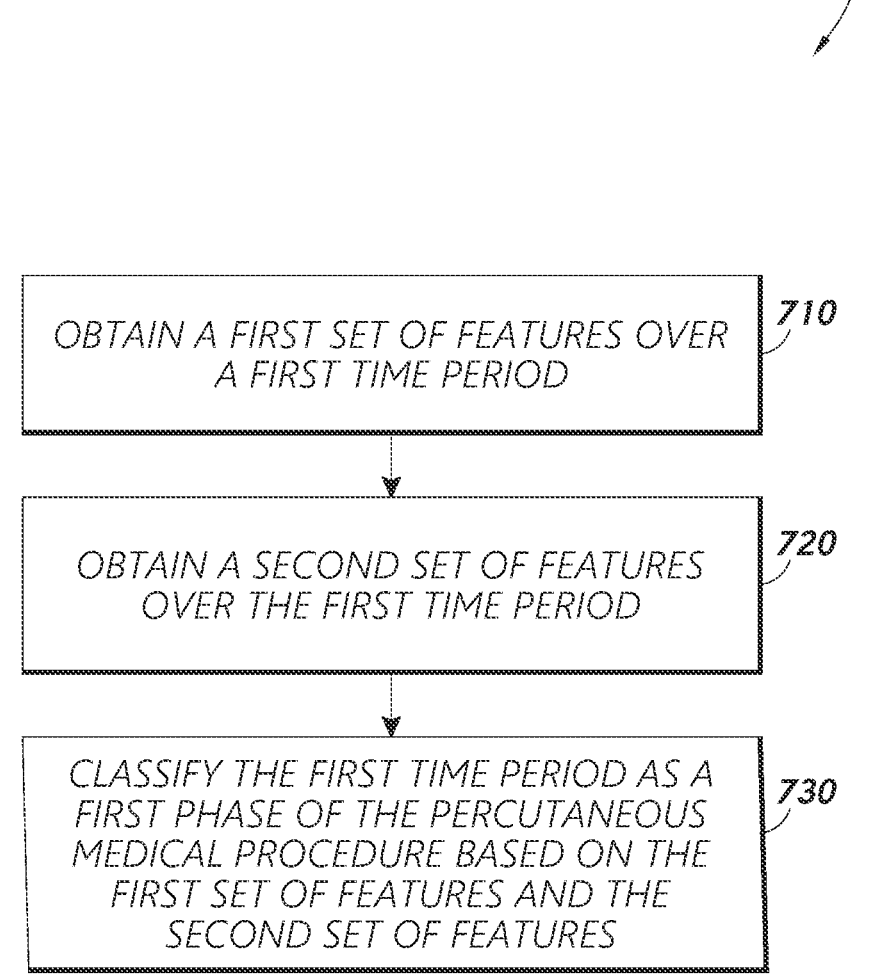
FIG. 7 is a flowchart showing a method to evaluate phases in a percutaneous medical procedure performed by a medical system, according to an example embodiment.

FIG. 7 is a flowchart showing a method 700 to segment a percutaneous medical procedure based on one or more determinable phases, according to an example embodiment. For ease in describing the method 700, the operations of the method 700 are described relative to the analytics engine 141A shown in FIG. 1. However, it is to be appreciated that the method 700 may be performed by any of the components, alone or in combination, discussed herein.

To begin the description of the method 700, at operation 710, the analytics engine 141A may obtain a first set of features over a first time period. The first set of features may be derived at least partially from instrument telemetry data corresponding to an endoluminal scope (e.g., scope 120). As described with reference to FIGS. 1-4, the scope instrument may be a robotically controlled instrument entering the patient's body through an endoluminal entrance, such as the urinary tract through the urethra. The scope telemetry features may include data derived from sensors attached to the scope (e.g., a location sensor, such as an EM sensor, shape sensor fiber, or the like) that characterizes one or more of: the position, orientation, movement of the scope instrument over time (e.g., the first time period). As discussed above, a feature extractor module may derive the scope instrument telemetry features from case logs generated by the medical system over the course of performing the medical procedure. The scope telemetry features may include scope position, scope orientation, relative needle scope heading, relative needle scope 3d distance, alignment error, scope linear body velocity, scope angular body velocity, scope absolute speed, and the like. These features and others are described in greater detail above.

At operation 720, the analytics engine 141A may obtain a second set of features over the first time period, the second set of features being derived at least in part from a percutaneous needle instrument. As described with reference to FIGS. 1-4, the needle instrument may be an instrument entering the patient's body percutaneously, such as through the skin of the flank of the patient. The needle telemetry features may be data derived from sensors attached to the needle (e.g., a location sensor, such as an EM sensor, shape sensor fiber, or the like) that characterizes one or more of: the position, orientation, movement of the needle instrument over time (e.g., the first time period). As discussed above, a feature extractor module may derive features related to the telemetry of the needle instrument from case logs generated by the medical system over the course of performing the medical procedure. The features related to the needle instrument telemetry may include needle position, needle orientation, relative needle scope heading, relative needle scope 3d distance, distance to target, distance to target plane, alignment error, needle linear body velocity, needle angular body velocity, needle absolute speed, and the like. These features and others are described in greater detail above.

At operation 730, the analytics engine 141A may classify at least a portion of the first time period as a first phase of the percutaneous medical procedure based on the first set of features and the second set of features. As discussed above, the percutaneous medical procedure can, depending on embodiment, include at least the following phases: needle insertion, target selection, site selection, and post needle insertion. In some embodiments, the classifier may generate classifications for multiple phases. In other embodiments, the classifier may generate binary classifications, e.g., needle insertion or not, where the Not classification signifies that the class may be any class other than a specified class. In some embodiments that generate binary classifications, the system may perform high-level decision mechanisms to reclassify the time periods associated with the Not classification, to uncover the phases of those time periods. Classification of time period may include identifying the start and end time of the classified phase. This may be accomplished by including a timestamp representing a time in which the phase begins. To identify the end of the classified phase, embodiments may include a duration associated with the classified phase or a timestamp representing a time in which the phase ends. Still further, some embodiments may represent the end of a phase based on an inference, such as the beginning of the next phase. In this inference approach, an embodiment may classify Phase1 as starting at Time1 and Phase2 starting at Time2. Embodiments may then infer that Phase1 ends when Phase2 begins (e.g., Time2).

Although not shown, the method 700 may have additional operations. For example, in some embodiments, operations 710, 720, and 730 could be performed with respect to additional time periods. In doing so, the method 700 obtains features from a different time period and then classifies at least a portion of that time period with another (potentially different) classification corresponding to a phase of the percutaneous medical procedure. This additional classification can be performed according to a many-to-one approach or a many-to-many approach. FIGS. 6C and 6D illustrate classification of the time period 600C and time period 600D associated with features derived from the telemetry data. However, it is to be appreciated that classification can use other case log data other than telemetry data and does not necessarily operate sequentially. Instead, some or all of the operations may be performed in parallel or otherwise overlapping. For example, in a many-to-many approach, all the phase classifications could be output at the same time based on case log data of the entire (or a significant portion of the) medical procedure.

In another example of an additional operation for the method 700 not shown in FIG. 7, an embodiment may obtain case log features related to a target, wherein the operation 730 further classifies the first time period with the classification based additionally on the case log features related to the target.

Example Phase-Based Analytics

Classifying the data from the system logs according to a phase in the percutaneous procedure may have a number of benefits. Such is the case because the information available to users from just the case logs may be limited to: the poses of instruments when field generator is in use, robot pose, and the pendant commands. Yet this information does not directly identify when needle insertion starts or how many attempts a user makes after selecting a target. The case logs also do not have direct data on what insertion site the user has selected. For example, to be able to compute the tract length, the anatomical position of the selected insertion sites, the system needs to know the pose of the needle, the position of the target, and "when" needle insertion starts. Embodiments discussed herein are capable of identifying what activity is going on in a procedure at a given time, so that the system can compute clinical metrics. Such metrics may be useable data for the physicians, as intraoperative data or as postoperative assessments. Furthermore, in some cases, data analytics on the metrics obtained over many medical procedures may uncover important factors that have impact on the success of a percutaneous procedure.

FIG. 8 is a flowchart showing a method 800 to generate clinical metrics in a percutaneous medical procedure, according to an example embodiment. For ease in describing the method 800, the operations of the method 800 are described relative to the analytics engine 141A shown in FIG. 1. However, it is to be appreciated that the method 800 may be performed by any of the components, alone or in combination, discussed herein.

To begin the discussion of the method 800, the analytics engine 141A obtains, at operation 810, telemetry data from one or more case logs of a first percutaneous procedure. As discussed, the telemetry data may characterize the sensor readings of a needle instrument over time. It is to be appreciated that, at operation 810, the analytics engine may receive additional data, such as robotic telemetry data, instrument telemetry data (e.g., sensor data), video data, device status data, and pendant command data.

At operation 820, the analytics engine 141A classifies a first time period associated with the telemetry data with a first phase of the percutaneous procedure based on the telemetry data. The classification performed in operation 820 may be performed using any of the classification methods discussed herein, such as using a machine learning approach that extracts features from the case log (or case logs) and evaluates them using a segmentation module, as shown in FIG. 5. Thus, although operation 820 is discussed as only classifying at least a portion of the first time period, it is to be appreciated that this disclosure contemplates embodiments that may classify multiple time periods. And further, such embodiments may classify the first time period or any other time period based on case log data corresponding to time periods outside of the first time period. For example, where a many-to-many approach is utilized, case log data covering the entire medical procedure may be used and estimates of the phases may be output at the same time.

At operation 830, the analytics engine 141, responsive to the first time period being associated with the first phase, generates clinical metrics associated the first phase in the percutaneous procedure from telemetry data corresponding to the first time period.

The types of metrics that can be generated by the analytics engine are now described. It is to be appreciated that these metrics may be generated for an individual procedure or can provide global insight by collecting data from many procedures and then generating historical averages or correlated metrics with successful procedures.

Target Selection Phase: number of targeted calyces, kidney survey time, pole, retraction distance (e.g., a distance the scope retracts after tagging the papilla), target selection duration, target offset from papilla, anterior vs posterior calyx, and parked pose.

Site Selection Phase: site selection time, average tract length, anatomical angles (e.g., cranial-caudal angle, anterior-posterior angle), distance of one or more instruments (e.g., scope or needle) with respect to a field generator, relative needle to scope angle, tract length, and angle to calyx (the angle between a measured needle trajectory and the orientation/heading of the calyx).

Needle Insertion Phase: success rate, needle insertion accuracy (as may be measured by a positional or angular deviation of the needle trajectory from a principal direction), needle insertion stability, shifts in scope position/heading, accuracy as measured by a UI element displayed to user, number of attempts, and needle insertion/retraction speed/acceleration.

In some embodiments, based on the clinical metrics generated at operation 830, the analytics engine may correlate those metrics with an impact to a procedure's success or failure. This may especially be the case for the cloud-based data analytics platform 149 shown in FIG. 1. This is the case because the cloud-based data analytics platform 149 obtains metrics across many different medical procedures. Based the correlations, an analytics engine (e.g., analytics engine 141A or analytics engine 141B) may provide pre-operative guidance, intraoperative guidance, or post-operative guidance that can inform the physician. Success can be determined automatically by the medical system. For example, an analytics engine may process the endoscopic video data to detect a needle instrument. In other embodiments, success can be determined manually or semi-automatically. For example, in the manual embodiments, a physician may input into the medical system that the percutaneous access procedure was successful or not. As another example, in the semi-automatic embodiments, a vision algorithm may detect a needle instrument in the scope camera data and request a user to confirm the success. It is to be further appreciated that success may not necessarily have a binary value but can also have a degree of success based on the location with the papilla that needle instrument has entered, and this can likewise be detected automatically by vision detection, manually detected, or semi-automatically.

Figure 9:
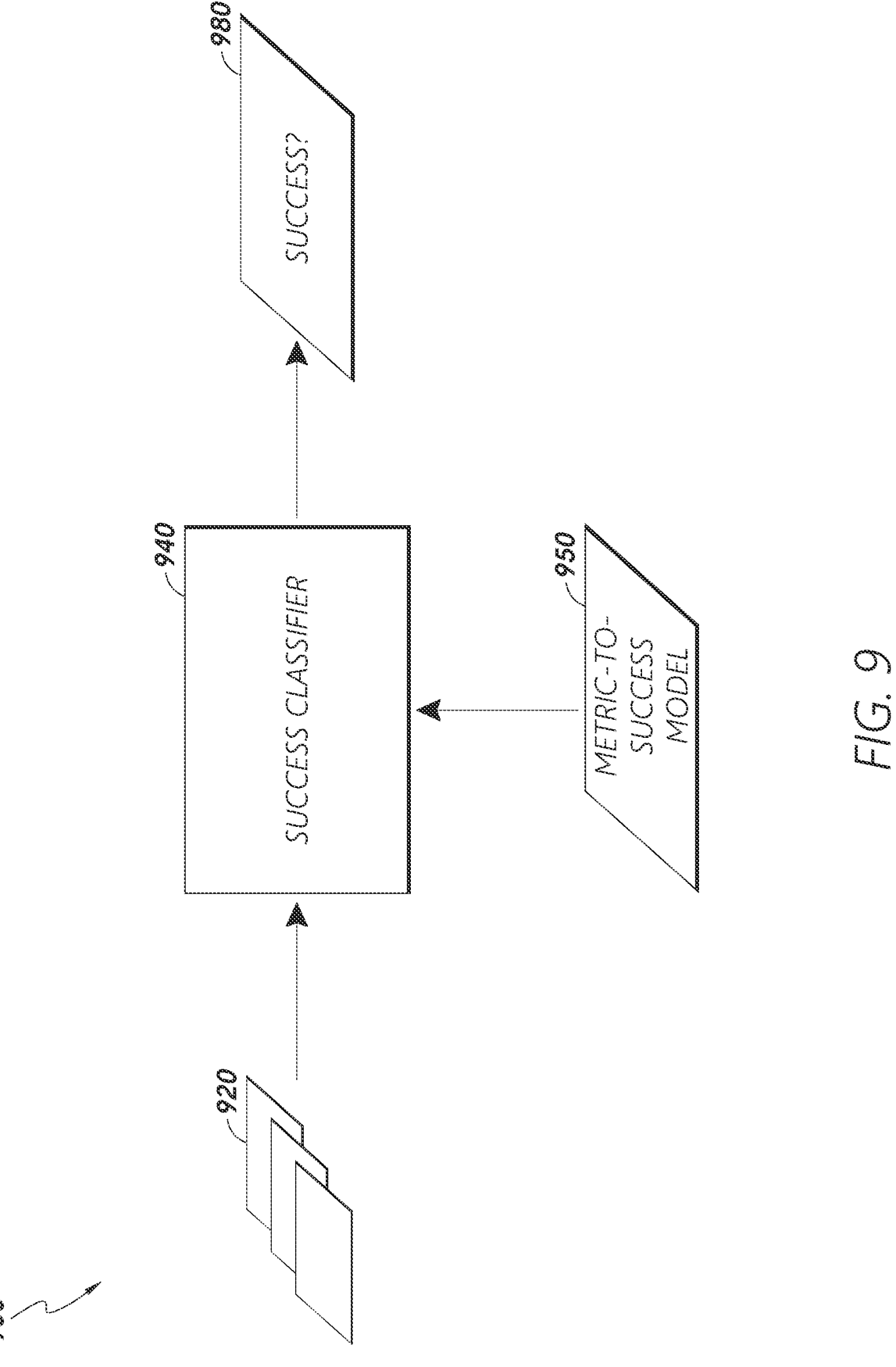
FIG. 9 is a block diagram illustrating an example success prediction system for generating predictions of a percutaneous medical procedure, according to example embodiments.

FIG. 9 is a block diagram illustrating an example success prediction system 900 for generating success predictions 980 of a percutaneous medical procedure, according to example embodiments. The success prediction system 900 may be implemented by any of the components described herein but, for clarity of description, will be discussed in the context of an analytics engine (e.g., analytics engine 141A or analytics engine 141B, shown in FIG. 1).

The success prediction system 900 may include a success classifier module 940. The success classifier module 940 may be a computer implemented module that receives one or more percutaneous case metrics 920 and outputs a success prediction 980 based on a metric-to-success model 950. The percutaneous case metrics 920 may include any of the metrics described above that may, for example, be computed after a percutaneous medical procedure has been segmented according to phase. The success prediction 980 may include any suitable indication of whether, given the percutaneous case metrics 920, the percutaneous procedure is likely to be successful or not. In some embodiments, the success prediction 980 may be given as a percentile, as a value corresponding to a class or rubric (e.g., an assigned grade), or any other suitable representation for a degree of success. In still other embodiments, the success prediction 980 may be presented as a 'heat map' with a probability of success of the percutaneous procedure at different positional insertion points and/or angles. For instance, a heat map may be displayed to the physician (e.g., on a display or user interface) using visual indications that show recommendations of approach(es) for the procedure that provide the greatest confidence in success.

In addition, a heat map may incorporate system variables that represent physical limitations of the robotic system, such as a length or a size of one or more instruments, or limitations of the robot's workspace. This function can also incorporate spatial information about the location of critical anatomical structures. For example, if a puncture site is outside of the robot' workspace or instrument reach, its probability can be set to zero to prevent the user from selecting an insertion site that may end up with procedure failure even though the user is able to gain a successful percutaneous access at this insertion site. In other embodiments, a heat map can be a direct function of the case metrics or give more weight to a subset of case metrics. For example, the input to the heat map can be restricted to only target selection metrics and site selection metrics or may give less weight to needle insertion metrics. In an example, the heat map may be based on data collected across multiple physicians and all patient populations. The heat map may also incorporate parameters that are optimized for a given physician or a given patient population to account for that physician's experience and the clinical specifications of that patient population.

The metric-to-success model 950 may be a model trained with the case metrics from a database of case data and success labels. In some embodiments, the metric-to-success model 950 may be based on a logistic regression framework. The case metrics may be derived from the case logs using embodiments discussed herein. A success label may be a label signifying whether a percutaneous procedure was a success or not, and may be labeled manually, automatically, or some combination thereof.

The success classifier module 940 discussed above learns how case metrics affect the success of an attempt. Using the success classifier module 940, embodiments can identify what values/range of values of these case metrics are correlated with a threshold success value (e.g., 50, 75, or 90% accuracy). For purposes of example, and not limitation, if the user wants to guarantee 75% of probability of success at the first attempt, embodiments of the success prediction system 900 may provide guidance that the angle to target should be a within a determinable angle, the scope should be within a determinable distance of the field generator, and the angle between needle and scope should be less than a determinable angle. The success prediction system 900 may provide additional guidance, some of which are now described.

It is to be appreciated that the success prediction system 900 can provide estimates for success based on any number of tailoring. At the highest level, embodiments may build the metric-to-success model 950 using data aggregated across different physicians, different operating sites, different robotic systems, and the like. Other embodiments may, additionally or alternatively, may build the metric-to-success model 950 with data that provides more tailored or specialized results. For example, the metric-to-success model 950 may include data that correlates physician-specific metrics with success. In this way, the success prediction system 900 can provide estimates (and as described below, guidance) on metrics that results in a particular physician achieving a given success result for a particular procedure. Thus, the success prediction system 900 may include different metric-to-success models, one for each physician that the system is to generate success estimates. This approach may be useful because physicians have different skill levels and may need different metrics to achieve a desired result. To illustrate, a physician with lower skill level/less experience may need to select an access point that has a smaller area than a physician with higher skill level, as the higher skilled physician may better navigate the needle through the patient body. Similarly, a higher skilled physician may be able to achieve success from a larger range of potential insertion points/angles that may have various levels of difficulty of navigation.

Another way embodiments may tailor success estimates is based on equipment used in a procedure. For example, some robotic systems may have sensors or control systems that result in higher accuracy in reaching a target, whereas systems with lessor sensor fidelity may provide feedback or control that reduces the likelihood of success. In these cases, the area for the needle insertion site for high success likelihood may differ among different robotic systems and embodiments discussed herein may account for these differences. Accordingly, the metric-to-success model 950 may include correlations between the metrics and success that also incorporate characteristics of the equipment used for the procedure.

Yet another way embodiments may tailor success estimates is based on characteristics of the patient. For example, patient bodies may differ based on age, gender, race, size, physiological metrics (e.g., heart rate, blood pressure, cholesterol reading, respiration rate, body temperature, blood oxygen, and the like), and any other suitable characteristic. Similar to above, the metric-to-success model 950 may include correlations between the metrics and success that also incorporate characteristics of the patient.

Although FIG. 9 has been discussed in relation to correlating metrics that result in a successful procedure, it is to be appreciated that embodiments may also generate correlations between metrics and adverse events, such as rupturing a patient's colon or any other organ. These types of correlations may allow embodiments to provide guidance on how to avoid adverse events or warning on when such occurrences are likely, within a determinable threshold.

Figure 10:
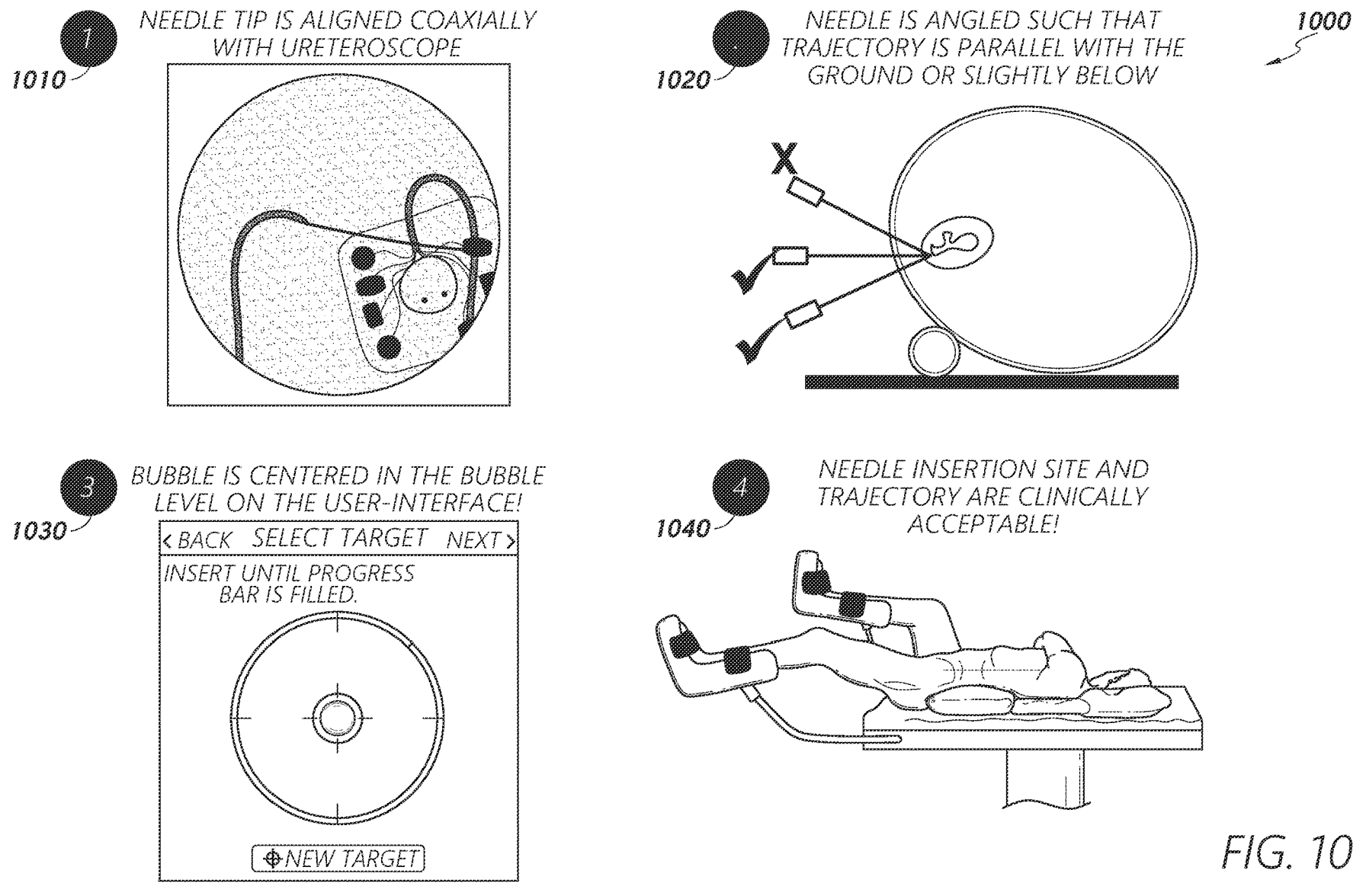

FIG. 10 is a diagram illustrating example guidance 1000 that may be provided according to example embodiments. The example guidance shown in FIG. 10 may be generated by a recommendation module (not shown) that receives a success prediction, such as the success prediction 980 shown in FIG. 9. Guidance 1010 may provide guidance on whether the needle tip is coaxially aligned with the scope within a sufficient threshold that is correlated with procedure success. Guidance 1020 may provide guidance on whether the anterior-posterior angle is within a sufficient threshold that is correlated with procedure success. Guidance 1030 may provide guidance on whether the insertion centering (e.g., steadiness) relative to a target is within a sufficient threshold that is correlated with procedure success. Guidance 1040 may provide guidance on whether the needle insertion site and trajectory are within a sufficient threshold that is correlated with procedure success. In an example embodiment, guidance 1040 may include indicators representing the likelihood of success for different needle insertion sites, as may be represented as heat maps, as described above.

It is to be appreciated that the guidance 1010, 1020, 1030, 1040 are provided by way of example and not limitation and other forms of guidance are within the contemplation of this disclosure. For example, in some embodiments, an analytics engine may provide alternate visual guidance, such as via a lighting pattern or color, or non-visual guidance, such as via sound or haptic feedback when the system detects one or more of the phase specific metrics is outside the bounds of a threshold that is correlated with procedure success. Additionally or alternatively, some embodiments may generate a likelihood for success in the procedure based on the phase-specific metrics and provide some feedback to the physician on that likelihood. Feedback on the likelihood of success may include a percentage, a color coding, a symbol, an audible alert, a haptic alert, and the like. Still further, some embodiments may use the metrics associated with a likelihood of success and automate some actions to achieve those metrics. An example of an automated response includes automatically positioning a robotic arm to achieve a desired needle trajectory or position the scope to achieve a desired target position and trajectory.

Other Classifying Approaches

Much of this disclosure thus far has focused on machine learning approaches for classifying the phases of a percutaneous procedure using data from case logs generated by a medical device system. However, it is to be appreciated that this disclosure contemplates that alternative or additional classification methodologies may be employed. Such approaches may be useful in automatically or semi-automatically labeling the training data used to build the models used by the medical system 100 for segmenting a percutaneous procedure into procedure phases. Additionally or alternatively, the approaches discussed in this section can be used as an engineered solution for classifying the percutaneous medical procedure in the segmentation modules.

Figure 11:
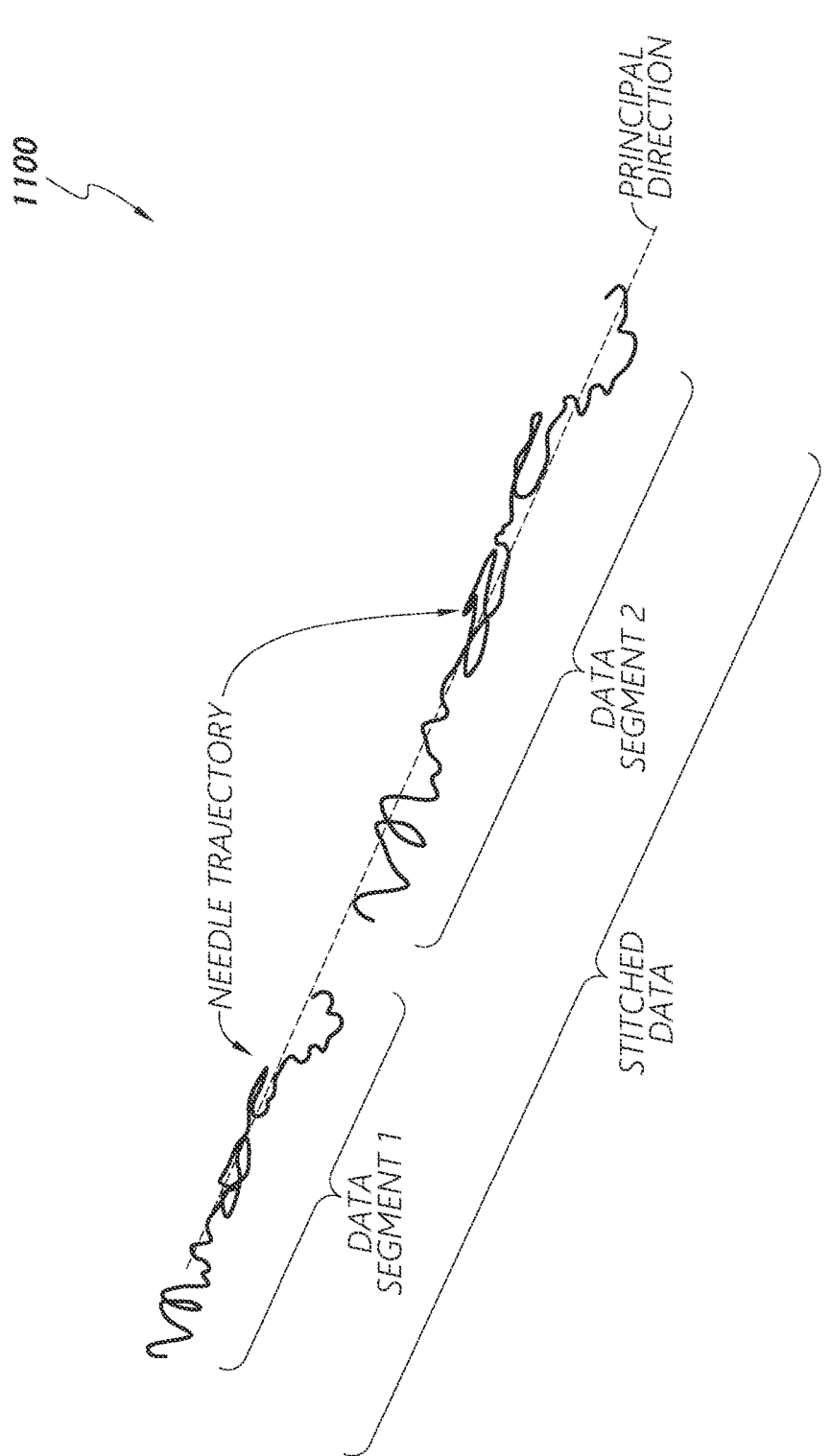
FIG. 11 is a diagram illustrating an example of needle electromagnetic data that may be labeled based at least in part with conditional logic, in accordance with example embodiments.

To detect Needle Insertion Phase, some embodiments of the analytics engine may process the EM logs and may evaluate certain conditions to label the data with the Needle Insertion Phase label. For example, the data analytics engine may use conditional logic to estimate needle insertion activity in the data. Such conditional logic includes: if the needle alignment error is less than a threshold, if distance to target is increasing, and needle position is changing along a principal axis or axis. If the condition is met, the time periods that met those criteria are labeled with the Needle Insertion phase. FIG. 11 is a diagram illustrating an example of needle EM data 1100 that may be labeled based at least in part with conditional logic, in accordance with example embodiments. As shown in FIG. 11, the EM data may include various segments that are stitched and then compared against a principal axis or direction.

Another approach for labeling the Needle Insertion Phase is to label some percentage of the training data (e.g., 25-50% of the training data, referred to as an "initial training data") manually and train a network to recognize needle insertion with the initial training data. The network trained with the initial training data may then be used to predict needle insertion in the remaining of the 50-75% of the cases and those predictions may be used in labeling the remaining 50-75% of the cases. A manual inspection of the labels generated from the model's predictions can be performed to make any necessary corrections.

The Target Selection Phase may be defined by tag and park events. The analytics engine may label the time frame between target selection and needle insertion to be site selection. The gaps between needle insertions and the idle time after the end of needle insertion labeled as post-insertion phase.

Example Robotic System

Figure 12:
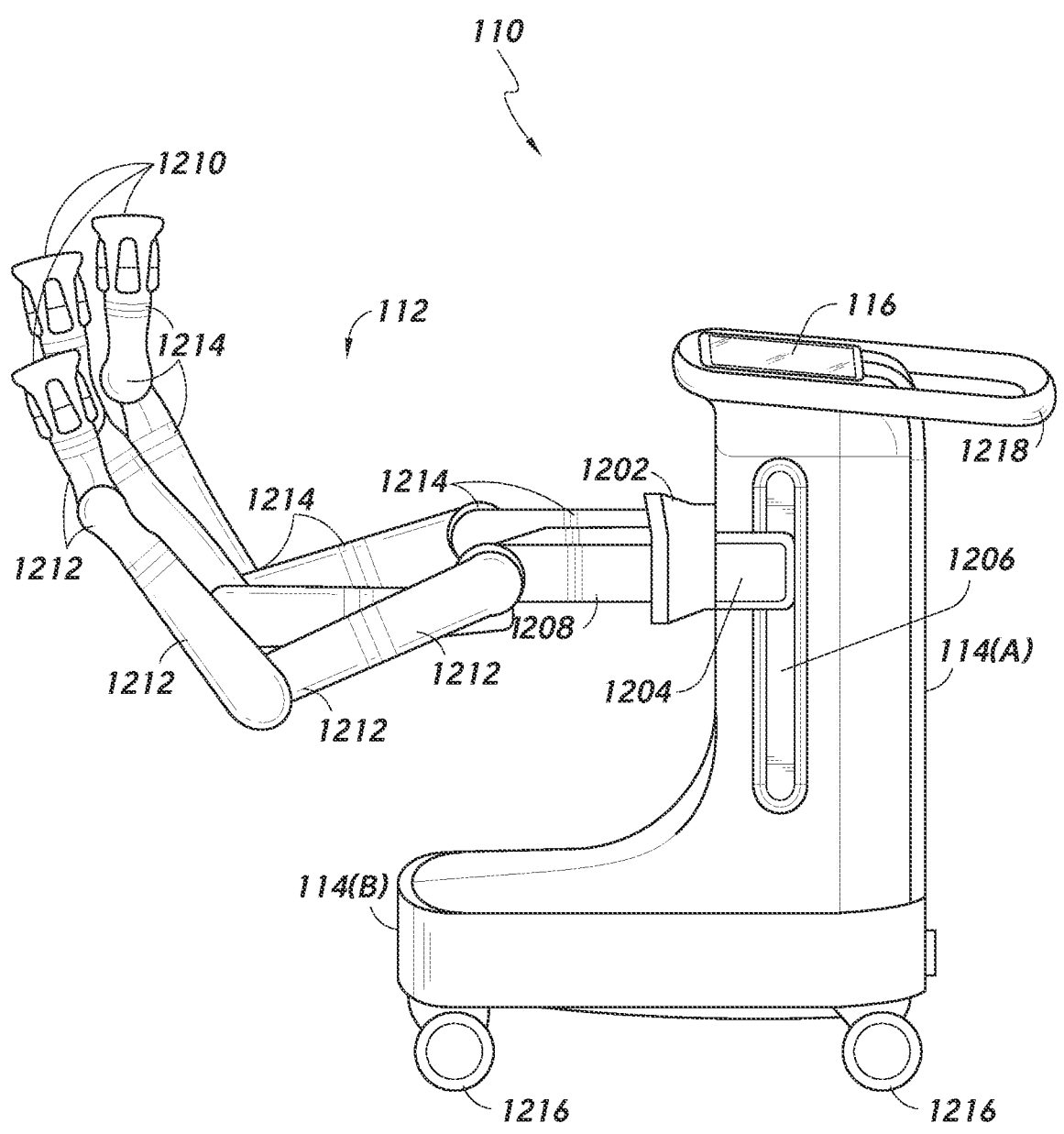
FIG. 12 illustrates example details of the robotic system of FIG. 1, in accordance with one or more embodiments.

FIG. 12 illustrates example details of the robotic system 110 in accordance with one or more embodiments. In this example, the robotic system 110 is illustrated as a cart-based robotically-enabled system that is movable. However, the robotic system 110 can be implemented as a stationary system, integrated into a table, and so on.

The robotic system 110 can include the support structure 114 including an elongated section 114(A) (sometimes referred to as "the column 114(A)") and a base 114(B). The column 114(A) can include one or more carriages, such as a carriage 1202 (alternatively referred to as "the arm support 1202") for supporting the deployment of one or more the robotic arms 112 (three shown in FIG. 12). The carriage 1202 can include individually configurable arm mounts that rotate along a perpendicular axis to adjust the base of the robotic arms 112 for positioning relative to a patient. The carriage 1202 also includes a carriage interface 1204 that allows the carriage 1202 to vertically translate along the column 114(A). The carriage interface 1204 is connected to the column 114(A) through slots, such as slot 1206, that are positioned on opposite sides of the column 114(A) to guide the vertical translation of the carriage 1202. The slot 1206 includes a vertical translation interface to position and hold the carriage 1202 at various vertical heights relative to the base 114(B). Vertical translation of the carriage 1202 allows the robotic system 110 to adjust the reach of the robotic arms 112 to meet a variety of table heights, patient sizes, physician preferences, etc. Similarly, the individually configurable arm mounts on the carriage 1202 allow a robotic arm base 1208 of the robotic arms 112 to be angled in a variety of configurations. The column 114(A) can internally comprise mechanisms, such as gears and/or motors, that are designed to use a vertically aligned lead screw to translate the carriage 1202 in a mechanized fashion in response to control signals generated in response to user inputs, such as inputs from the I/O device(s) 116.

In some embodiments, the slot 1206 can be supplemented with a slot cover(s) that is flush and/or parallel to the slot surface to prevent dirt and/or fluid ingress into the internal chambers of the column 114(A) and/or the vertical translation interface as the carriage 1202 vertically translates. The slot covers can be deployed through pairs of spring spools positioned near the vertical top and bottom of the slot 1206. The covers can be coiled within the spools until deployed to extend and retract from their coiled state as the carriage 1202 vertically translates up and down. The spring-loading of the spools can provide force to retract the cover into a spool when the carriage 1202 translates towards the spool, while also maintaining a tight seal when the carriage 1202 translates away from the spool. The covers can be connected to the carriage 1202 using, for example, brackets in the carriage interface 1204 to ensure proper extension and retraction of the covers as the carriage 1202 translates.

The base 114(B) can balance the weight of the column 114(A), the carriage 1202, and/or robotic arms 112 over a surface, such as the floor. Accordingly, the base 114(B) can house heavier components, such as one or more of electronics, motors, power supply, etc., as well as components that enable movement and/or immobilize the robotic system 110. For example, the base 114(B) can include rollable wheels (also referred to as "the casters 1216") that allow for the robotic system 110 to move around the room for a procedure. After reaching an appropriate position, the casters 1216 can be immobilized using wheel locks to hold the robotic system 110 in place during the procedure. As shown, the robotic system 110 also includes a handle 1218 to assist with maneuvering and/or stabilizing the robotic system 110.

The robotic arms 112 can generally comprise robotic arm bases 1208 and end effectors 1210, separated by a series of linkages 1212 that are connected by a series of joints 1214. Each joint 1214 can comprise an independent actuator and each actuator can comprise an independently controllable motor. Each independently controllable joint 1214 represents an independent degree of freedom available to the robotic arm 112. For example, each of the robotic arms 112 can have seven joints, and thus, provide seven degrees of freedom. However, any number of joints can be implemented with any degrees of freedom. In examples, a multitude of joints can result in a multitude of degrees of freedom, allowing for "redundant" degrees of freedom. Redundant degrees of freedom allow the robotic arms 112 to position their respective end effectors 1210 at a specific position, orientation, and/or trajectory in space using different linkage positions and/or joint angles. In some embodiments, the end effectors 1210 can be configured to engage with and/or control a medical instrument, a device, an object, and so on. The freedom of movement of the robotic arms 112 can allow the robotic system 110 to position and/or direct a medical instrument from a desired point in space and/or allow a physician to move the robotic arms 112 into a clinically advantageous position away from the patient to create access, while avoiding arm collisions.

As shown in FIG. 12, the robotic system 110 can also include the I/O device(s) 116. The I/O device(s) 116 can include a display, a touchscreen, a touchpad, a projector, a mouse, a keyboard, a microphone, a speaker, a controller, a camera (e.g., to receive gesture input), or another I/O device to receive input and/or provide output. The I/O device(s) 116 can be configured to receive touch, speech, gesture, or any other type of input. The I/O device(s) 116 can be positioned at the vertical end of column 114(A) (e.g., the top of the column 114(A)) and/or provide a user interface for receiving user input and/or for providing output. For example, the I/O device(s) 116 can include a touchscreen (e.g., a dual-purpose device) to receive input and provide a physician with pre-operative and/or intra-operative data. Example pre-operative data can include pre-operative plans, navigation, and/or mapping data derived from pre-operative computerized tomography (CT) scans, and/or notes from pre-operative patient interviews. Example intra-operative data can include optical information provided from a tool/instrument, sensor, and/or coordinate information from sensors, as well as vital patient statistics, such as respiration, heart rate, and/or pulse. The I/O device(s) 116 can be positioned and/or tilted to allow a physician to access the I/O device(s) 116 from a variety of positions, such as the side of the column 114(A) opposite the carriage 1202. From this position, the physician can view the I/O device(s) 116, the robotic arms 112, and/or a patient while operating the I/O device(s) 116 from behind the robotic system 110.

The robotic system 110 can include a variety of other components. For example, the robotic system 110 can include one or more control electronics/circuitry, power sources, pneumatics, optical sources, actuators (e.g., motors to move the robotic arms 112), memory, and/or communication interfaces (e.g. to communicate with another device). In some embodiments, the memory can store computer-executable instructions that, when executed by the control circuitry, cause the control circuitry to perform any of the operations discussed herein. For example, the memory can store computer-executable instructions that, when executed by the control circuitry, cause the control circuitry to receive input and/or a control signal regarding manipulation of the robotic arms 112 and, in response, control the robotic arms 112 to be positioned in a particular arrangement and/or to navigate a medical instrument connected to the end effectors 1210.

In some embodiments, robotic system 110 is configured to engage with and/or control a medical instrument, such as the scope 120. For example, the robotic arms 112 can be configured to control a position, orientation, and/or tip articulation of a scope (e.g., a sheath and/or a leader of the scope). In some embodiments, the robotic arms 112 can be configured/configurable to manipulate the scope 120 using elongate movement members. The elongate movement members can include one or more pull wires (e.g., pull or push wires), cables, fibers, and/or flexible shafts. To illustrate, the robotic arms 112 can be configured to actuate multiple pull wires coupled to the scope 120 to deflect the tip of the scope 120. Pull wires can include any suitable or desirable materials, such as metallic and/or non-metallic materials such as stainless steel, Kevlar, tungsten, carbon fiber, and the like. In some embodiments, the scope 120 is configured to exhibit nonlinear behavior in response to forces applied by the elongate movement members. The nonlinear behavior can be based on stiffness and compressibility of the scope 120, as well as variability in slack or stiffness between different elongate movement members.

Example Control System

Figure 13:
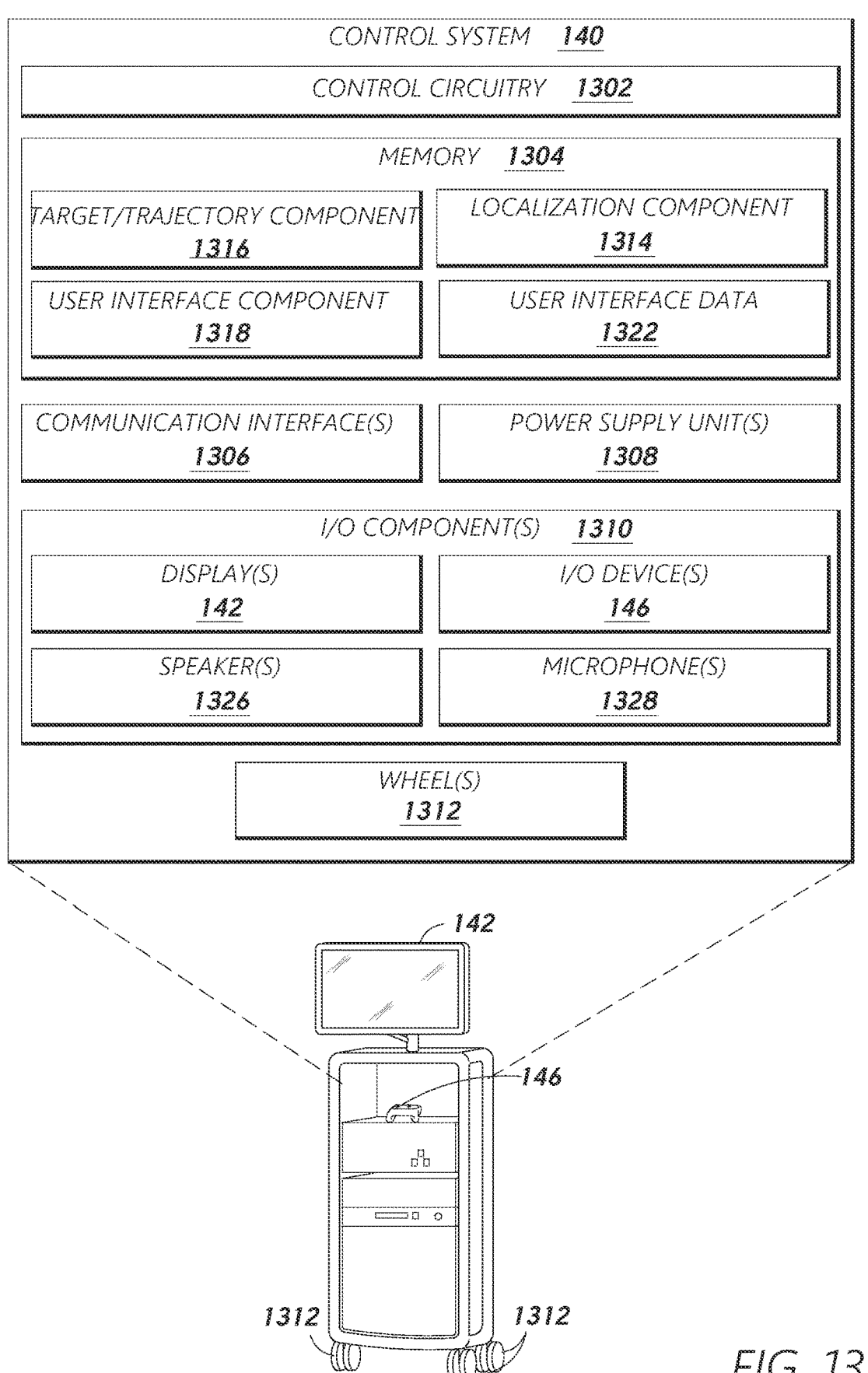
FIG. 13 illustrates example details of the control system of FIG. 1, in accordance with one or more embodiments.

FIG. 13 illustrates example details of the control system 140 in accordance with one or more embodiments. As illustrated, the control system 140 can include one or more of the following components, devices, modules, and/or units (referred to herein as "components"), either separately/individually and/or in combination/collectively: control circuitry 1302, data storage/memory 1304, one or more communication interfaces 1306, one or more power supply units 1308, one or more I/O components 1310, and/or one or more wheels 1312 (e.g., casters or other types of wheels). In some embodiments, the control system 140 can comprise a housing/enclosure configured and/or dimensioned to house or contain at least part of one or more of the components of the control system 140. In this example, the control system 140 is illustrated as a cart-based system that is movable with the one or more wheels 1312. In some cases, after reaching the appropriate position, the one or more wheels 1312 can be immobilized using wheel locks to hold the control system 140 in place. However, the control system 140 can be implemented as a stationary system, integrated into another system/device, and so on.

Although certain components of the control system 140 are illustrated in FIG. 13, it should be understood that additional components not shown can be included in embodiments in accordance with the present disclosure. Furthermore, certain of the illustrated components can be omitted in some embodiments. Although the control circuitry 1302 is illustrated as a separate component in the diagram of FIG. 13, it should be understood that any or all of the remaining components of the control system 140 can be embodied at least in part in the control circuitry 1302. That is, the control circuitry 1302 can include various devices (active and/or passive), semiconductor materials and/or areas, layers, regions, and/or portions thereof, conductors, leads, vias, connections, and/or the like, wherein one or more of the other components of the control system 140 and/or portion(s) thereof can be formed and/or embodied at least in part in/by such circuitry components/devices.

The various components of the control system 140 can be electrically and/or communicatively coupled using certain connectivity circuitry/devices/features, which can or may not be part of the control circuitry 1302. For example, the connectivity feature(s) can include one or more printed circuit boards configured to facilitate mounting and/or interconnectivity of at least some of the various components/circuitry of the control system 140. In some embodiments, two or more of the control circuitry 1302, the data storage/memory 1304, the communication interface(s) 1306, the power supply unit(s) 1308, and/or the input/output (I/O) component(s) 1310, can be electrically and/or communicatively coupled to each other.

As illustrated, the memory 1304 can include a localization component 1314, a target/trajectory component 1316, and a user interface component 1318 configured to facilitate various functionality discussed herein. In some embodiments, the localization component 1314, the target/trajectory component 1316, and/or the user interface component 1318 can include one or more instructions that are executable by the control circuitry 1302 to perform one or more operations. Although many embodiments are discussed in the context of the components 1314-1318 including one or more instructions that are executable by the control circuitry 1302, any of the components 1314-1318 can be implemented at least in part as one or more hardware logic components, such as one or more application specific integrated circuits (ASIC), one or more field-programmable gate arrays (FPGAs), one or more application-specific standard products (ASSPs), one or more complex programmable logic devices (CPLDs), and/or the like. Furthermore, although the components 1314-1318 are illustrated as being included within the control system 140, any of the components 1314-1318 can be implemented at least in part within another device/system, such as the robotic system 110, the table 150, or another device/system. Similarly, any of the other components of the control system 140 can be implemented at least in part within another device/system.

The localization component 1314 can be configured to perform one or more localization techniques to determine and/or track a position and/or an orientation of an object, such as a medical instrument. For example, the localization component 1314 can process input data (e.g., sensor data from a medical instrument, model data regarding anatomy of a patient, position data of a patient, pre-operative data, robotic command and/or kinematics data, etc.) to generate position/orientation data for one or more medical instruments. The position/orientation data can indicate a location and/or an orientation of one or more medical instruments relative to a frame of reference. The frame of reference can be a frame of reference relative to anatomy of a patient, a known object (e.g., an EM field generator), a coordinate system/space, and so on. In some implementations, the position/orientation data can indicate a location and/or an orientation of a distal end of a medical instrument (and/or proximal end, in some cases).

In some embodiments, the localization component 1314 can process pre-operative data to determine a position and/or an orientation of an object. The pre-operative data (sometimes referred to as "mapping data") can be generated by performing computed tomography (CT) scans, such as low dose CT scans. The pre-operative CT images from the scans can be reconstructed into three-dimensional images, which are visualized, e.g., as "slices" of a cutaway view of a patient's internal anatomy. When analyzed in the aggregate, image-based models for anatomical cavities, spaces, and/or structures of the patient's anatomy, such as a patient lung network, can be generated. A center-line geometry can be determined and/or approximated from the CT images to develop a three-dimensional volume of the patient's anatomy, referred to as model data (also referred to as "pre-operative model data" when generated using only pre-operative CT scans). Example uses of center-line geometry are discussed in U.S. patent application Ser. No. 14/523,760, the contents of which are herein incorporated by reference in its entirety. Network topological models can also be derived from CT-images.

Further, in some embodiments, the localization component 1314 can perform vision-based techniques to determine a position and/or an orientation of an object. For example, a medical instrument can be equipped with a camera, a range sensor (sometimes referred to as "a depth sensor"), a radar device, etc., to provide sensor data in the form of vision data. The localization component 1314 can process the vision data to facilitate vision-based location tracking of the medical instrument. For example, a pre-operative model data can be used in conjunction with vision data to enable computer vision-based tracking of a medical instrument (e.g., an endoscope). In examples, using pre-operative model data, the control system 140 can generate a library of expected endoscopic images based on the expected path of travel of a scope, with each image being linked to a location within the model. Intra-operatively, this library can be referenced by the control system 140 in order to compare real-time images and/or other vision data captured at a scope (e.g., a camera at a distal end of an endoscope) to those in the image library to assist with localization.

Moreover, in some embodiments, other types of vision-based techniques can be performed to determine a position and/or an orientation of an object. For example, the localization component 1314 can use feature tracking to determine motion of an image sensor (e.g., a camera or other sensor), and thus, a medical instrument associated with the image sensor. In some cases, the localization component 1314 can identify circular geometries in pre-operative model data that correspond to anatomical lumens and track the change of those geometries to determine which anatomical lumen was selected, as well as the relative rotational and/or translational motion of the medical instrument. Use of a topological map can also enhance vision-based algorithms or techniques. Furthermore, the localization component 1314 can use optical flow, another computer vision-based technique, to analyze displacement and/or translation of image pixels in a video sequence in vision data to infer camera movement. Examples of optical flow techniques can include motion detection, object segmentation calculations, luminance, motion compensated encoding, stereo disparity measurement, etc. By comparing multiple frames over multiple iterations, the localization component 1314 can determine movement and a location of an image sensor (and thus an endoscope).

Furthermore, in some embodiments, the localization component 1314 can use electromagnetic tracking to determine a position and/or an orientation of an object. For example, the localization component 1314 can use real-time EM tracking to determine a real-time location of a medical instrument in a coordinate system/space that can be registered to the patient's anatomy, which can be represented by a pre-operative model or other model. In EM tracking, an EM sensor (or tracker) including one or more sensor coils can be embedded in one or more locations and/or orientations in a medical instrument (e.g., a scope, a needle, etc.). The EM sensor can measure a variation in an EM field created by one or more static EM field generators positioned at a known location. The location information detected by the EM sensors can be stored as EM data. The localization component 1314 can process the EM data to determine a position and/or orientation of an object, such as a medical instrument. An EM field generator (or transmitter) can be placed close to the patient (e.g., within a predetermined distance) to create a low intensity magnetic field that an EM sensor can detect. The magnetic field can induce small currents in the sensor coils of the EM sensor, which can be analyzed to determine a distance and/or angle between the EM sensor and the EM field generator. These distances and/or orientations can be intra-operatively "registered" to patient anatomy (e.g., a pre-operative model) in order to determine a geometric transformation that aligns a single location in a coordinate system with a position in the pre-operative model of the patient's anatomy. Once registered, an EM sensor (e.g., an embedded EM tracker) in one or more positions of a medical instrument (e.g., the distal tip of an endoscope, a needle, etc.) can provide real-time indications of a position and/or an orientation the medical instrument through the patient's anatomy.

Additionally or alternatively, in some embodiments, the localization component 1314 can use robotic command and/or kinematics data to determine a position and/or an orientation of an object. Robotic command and/or kinematics data can be indicative of pitch and/or yaw (e.g., of a robotic arm) resulting from an articulation command, such as those used during pre-operative calibration and/or during a procedure. Intra-operatively, calibration measurements can be used in combination with known insertion depth information to estimate a position and/or an orientation of a medical instrument. Alternatively or additionally, these calculations can be analyzed in combination with EM, vision, and/or topological modeling to estimate a position and/or orientation of a medical instrument.

Further, in some embodiments, the localization component 1314 can use other types of data to determine a position and/or an orientation of an object. For example, the localization component 1314 can analyze sensor data from a shape sensing fiber (e.g., which can provide shape data regarding a location/shape of a medical instrument), an accelerometer, a gyroscope, a satellite-based positioning sensor (e.g., a global positioning system (GPS)), a radio-frequency transceiver, and so on, embedded on a medical instrument. Such data can be indicative of a position and/or an orientation of the medical instrument.

In some embodiments, the localization component 1314 can use input data in combination. For example, the localization component 1314 can use a probabilistic approach where a confidence weight is assigned to a position/orientation determined from multiple forms of input data. To illustrate, if EM data is not as reliable (as may be the case where there is EM interference), the EM data can be associated with a relatively low confidence value and other forms of input data can be relied on, such as vision data, robotic command and kinematics data, and so on.

The target/trajectory component 1316 can be configured to determine a position of a target location within the human anatomy and/or a coordinate space/system. A target location can represent a point/point set within the human anatomy and/or a coordinate space/system. For example, the target/trajectory component 1316 can identify one or more points for a target location within a coordinate system, identify coordinates for the one or more points (e.g., X, Y, Z coordinates for each point), and associate the coordinates with the target location. In some embodiments, the target/trajectory component 1316 can use a position and/or orientation of a medical instrument to determine a position of a target location. For example, a scope can be navigated to contact or be within proximity to a target location (e.g., parked in-front of the target location). The localization component 1314 can use localization techniques to determine a position of the scope (e.g., a location of the end of the scope) and/or a position of an object within a field-of-view of the scope. The target/trajectory component 1316 can associate the position of the scope (e.g., the coordinates of the scope) with the target location. Additionally or alternatively, in some embodiments, a scope can deliver a fiduciary to mark a target location and a position of the fiduciary can be determined.

A target location can represent a fixed or movable point(s) within the human anatomy and/or a coordinate space/system. For example, if a papilla is initially designated as a target location, coordinates for the target location can be determined and updated as the procedure proceeds and the papilla moves (e.g., due to insertion of a medical instrument). Here, a location of a scope (which can be within proximity to the papilla) can be tracked over time and used to update the coordinates of the target location. In some embodiments, the target/trajectory component 1316 can estimate/predict a position of a target location. Here, the target location can be represented with the predicted position. For example, the target/trajectory component 1316 can use an algorithm to predict coordinates of the target location as the human anatomy moves. The predicted coordinates can be used to determine a target trajectory.

The target/trajectory component 1316 can also be configured to determine a target trajectory for a medical instrument or another object. A target trajectory can represent a desired path for accessing a target location. A target trajectory can be determined based on a variety of information, such as a position of a medical instrument(s) (e.g., a needle, a scope, etc.), a target location within the human anatomy, a position and/or orientation of a patient, the anatomy of the patient (e.g., the location of organs within the patient relative to the target location), and so on. For example, a target trajectory can include a line that extends from a position of a medical instrument and/or a location on the skin of a patient to/through a position of a target location within the patient. In examples, a physician can analyze images or models of the human anatomy and provide input to designate a target trajectory, such as by drawing a line on an image of the internal anatomy of a patient. In some embodiments, the target/trajectory component 1316 can calculate a target trajectory initially and/or update the target trajectory throughout the procedure. For example, as a target location moves during the procedure, a target trajectory can be updated due to the change in position of the target location. In examples where a target location is estimated, a target trajectory can represent an estimated path to reach the target location.

In some embodiments, a target trajectory and/or a trajectory of a medical instrument can be defined/represented with respect to one or more anatomical planes/axes. For example, a trajectory can be defined/represented as an angle with respect to the coronal/sagittal/transverse plane(s) or another plane/axis (e.g., a 20 degree cranial-caudal angle, 10 degree medial-lateral angle, etc.). To illustrate, the control system 140 can determine a pose of a medical instrument with respect to an EM field generator and/or a location of a target with respect to the EM field generator. The control system 140 can also determine, based on robotic kinematics, a pose of the EM field generator with respect to a robotic system. In some cases, the control system 140 can infer/determine that the robotics system is parallel to the bed. Based on such information, the control system 140 can determine a target trajectory and/or a trajectory of the medical instrument within respect to an anatomical plane, such as an angle with respect to an anatomical plane for the patient on the bed.

The user interface component 1318 can be configured to facilitate one or more user interfaces (also referred to as "one or more graphical user interfaces (GUI)"). For example, the user interface component 1318 can generate user interface data 1322 representing an instrument-alignment interface that includes one or more visualizations to indicate an orientation and/or position of a medical instrument. The user interface component 1318 can use the position/orientation data regarding a medical instrument, information regarding a target location, and/or information regarding a target trajectory to present, within the instrument-alignment interface, one or more visualizations indicative of an alignment of an orientation of the medical instrument relative to the target trajectory and/or a proximity of the medical instrument to the target location. Further, the user interface component 1318 can use vision data, such as images captured by a scope, to present information within the instrument-alignment interface. In examples, information can be overlaid on images from a scope (e.g., augmented image view). The user interface component 1318 can provide the user interface data 1322 or other data to the one or more displays 142 and/or another display(s) for display of the instrument-alignment interface.

The one or more communication interfaces 1306 can be configured to communicate with one or more device/sensors/systems. For example, the one or more communication interfaces 1306 can send/receive data in a wireless and/or wired manner over a network. A network in accordance with embodiments of the present disclosure can include a local area network (LAN), wide area network (WAN) (e.g., the Internet), personal area network (PAN), body area network (BAN), etc. In some embodiments, the one or more communication interfaces 1306 can implement a wireless technology such as Bluetooth, Wi-Fi, near field communication (NFC), or the like.

The one or more power supply units 1308 can be configured to manage power for the control system 140 (and/or the robotic system 110, in some cases). In some embodiments, the one or more power supply units 1308 include one or more batteries, such as a lithium-based battery, a lead-acid battery, an alkaline battery, and/or another type of battery. That is, the one or more power supply units 1308 can comprise one or more devices and/or circuitry configured to provide a source of power and/or provide power management functionality. Moreover, in some embodiments the one or more power supply units 1308 include a mains power connector that is configured to couple to an alternating current (AC) or direct current (DC) mains power source.

The one or more I/O components 1310 can include a variety of components to receive input and/or provide output, such as to interface with a user. The one or more I/O components 1310 can be configured to receive touch, speech, gesture, or any other type of input. In examples, the one or more I/O components 1310 can be used to provide input regarding control of a device/system, such as to control the robotic system 110, navigate the scope or other medical instrument attached to the robotic system 110, control the table 150, control the imaging device 190, and so on. As shown, the one or more I/O components 1310 can include the one or more displays 142 (sometimes referred to as "the one or more display devices 142") configured to display data. The one or more displays 142 can include one or more liquid-crystal displays (LCD), light-emitting diode (LED) displays, organic LED displays, plasma displays, electronic paper displays, and/or any other type(s) of technology. In some embodiments, the one or more displays 142 include one or more touchscreens configured to receive input and/or display data. Further, the one or more I/O components 1310 can include the one or more I/O devices 146, which can include a touchscreen, touch pad, controller, mouse, keyboard, wearable device (e.g., optical head-mounted display), virtual or augmented reality device (e.g., head-mounted display), etc. Additionally, the one or more I/O components 1310 can include one or more speakers 1326 configured to output sounds based on audio signals and/or one or more microphones 1328 configured to receive sounds and generate audio signals. In some embodiments, the one or more I/O components 1310 include or are implemented as a console.

Although not shown in FIG. 13, the control system 140 can include and/or control other components, such as one or more pumps, flow meters, valve controls, and/or fluid access components in order to provide controlled irrigation and/or aspiration capabilities to a medical instrument (e.g., a scope), a device that can be deployed through a medical instrument, and so on. In some embodiments, irrigation and aspiration capabilities can be delivered directly to a medical instrument through separate cable(s). Further, the control system 140 can include a voltage and/or surge protector designed to provide filtered and/or protected electrical power to another device, such as the robotic system 110, thereby avoiding placement of a power transformer and other auxiliary power components in robotic system 110, resulting in a smaller, more moveable robotic system 110.

The control system 140 can also include support equipment for sensors deployed throughout the medical system 100. For example, the control system 140 can include opto-electronics equipment for detecting, receiving, and/or processing data received from optical sensors and/or cameras. Such opto-electronics equipment can be used to generate real-time images for display in any number of devices/systems, including in the control system 140. Similarly, the control system 140 can include an electronic subsystem for receiving and/or processing signals received from deployed electromagnetic (EM) sensors. In some embodiments, the control system 140 can also be used to house and position an EM field generator for detection by EM sensors in or on a medical instrument.

In some embodiments, the control system 140 can be coupled to the robotic system 110, the table 150, and/or a medical instrument, such as the scope 120 and/or the needle 170, through one or more cables or connections (not shown). In some implementations, support functionality from the control system 140 can be provided through a single cable, simplifying and de-cluttering an operating room. In other implementations, specific functionality can be coupled in separate cabling and connections. For example, while power can be provided through a single power cable, the support for controls, optics, fluidics, and/or navigation can be provided through a separate cable.

The term "control circuitry" is used herein according to its broad and ordinary meaning, and can refer to any collection of one or more processors, processing circuitry, processing modules/units, chips, dies (e.g., semiconductor dies including come or more active and/or passive devices and/or connectivity circuitry), microprocessors, micro-controllers, digital signal processors, microcomputers, central processing units, graphics processing units, field programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry can further comprise one or more, storage devices, which can be embodied in a single memory device, a plurality of memory devices, and/or embedded circuitry of a device. Such data storage can comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware state machine (and/or implements a software state machine), analog circuitry, digital circuitry, and/or logic circuitry, data storage device(s)/register(s) storing any associated operational instructions can be embedded within, or external to, the circuitry comprising the state machine, analog circuitry, digital circuitry, and/or logic circuitry.

The term "memory" is used herein according to its broad and ordinary meaning and can refer to any suitable or desirable type of computer-readable media. For example, computer-readable media can include one or more volatile data storage devices, non-volatile data storage devices, removable data storage devices, and/or nonremovable data storage devices implemented using any technology, layout, and/or data structure(s)/protocol, including any suitable or desirable computer-readable instructions, data structures, program modules, or other types of data.

Computer-readable media that can be implemented in accordance with embodiments of the present disclosure includes, but is not limited to, phase change memory, static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device. As used in certain contexts herein, computer-readable media may not generally include communication media, such as modulated data signals and carrier waves. As such, computer-readable media should generally be understood to refer to non-transitory media.

ADDITIONAL EMBODIMENTS

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is understood with the context as used in general to convey that an item, term, element, etc. may be either X, Y, or Z. Thus, such conjunctive language is not generally intended to imply that certain embodiments require at least one of X, at least one of Y, and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the disclosure should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A method of segmenting a percutaneous medical procedure based on one or more determinable phases, the method comprising:

obtaining a first set of features over a first time period, the first set of features being derived from scope telemetry data corresponding to an endoluminal scope instrument;

obtaining a second set of features over the first time period, the second set of features being derived from needle telemetry data corresponding to a percutaneous needle instrument; and classifying at least one portion of the first time period as a first phase of the percutaneous medical procedure based on the first set of features, the second set of features, and telemetry data received from a medical system while performing a prior percutaneous medical procedure on a physical anatomy.

2. The method of claim 1, wherein the endoluminal scope instrument includes a location sensor, and wherein the first set of features includes data derived from the location sensor.

3. The method of claim 1, wherein the first phase corresponds to a binary classification that includes a needle insertion class.

4. The method of claim 1, wherein classifying the at least one portion of the first time period comprises:

indicating a beginning of an attempt to insert the percutaneous needle instrument towards a target location through a percutaneous entrance; and indicating an end of the attempt to insert the percutaneous needle instrument towards the target location through the percutaneous entrance.

5. The method of claim 1, further comprising:

obtaining a third set of features over a second time period, the third set of features being derived from the scope telemetry data;

obtaining a fourth set of features over the second time period, the fourth set of features being derived from the needle telemetry data; and based on the third set of features and the fourth set of features, classifying at least a portion of the second time period as a second phase of the percutaneous medical procedure.

6. The method of claim 5, wherein the first phase and the second phase are different phases of the percutaneous medical procedure.

7. The method of claim 5, wherein the first phase and the second phase are a same phase of the percutaneous medical procedure.

8. The method of claim 5, wherein the first set of features and the third set of features are associated with a feature segment, and wherein the first time period and the second time period are classified by a single model evaluation of the feature segment.

9. The method of claim 5, wherein the first set of features is associated with a first windowed segment and the third set of features is associated with a second windowed segment, and wherein classifying the first time period includes sending the first windowed segment to a first model evaluation block and classifying the second time period includes sending the second windowed segment to a second model evaluation block.

10. The method of claim 1, wherein the first set of features includes at least one of a scope position, a scope orientation, a relative needle scope heading, a relative needle scope three-dimensional (3D) distance, an alignment error, a scope linear body velocity, a scope angular body velocity, or a scope absolute speed.

11. The method of claim 1, wherein the second set of features includes at least one of a needle position, a needle orientation, a relative needle scope heading, a relative needle scope three-dimensional (3D) distance, a distance to target, a distance to target plane, an alignment error, a needle linear body velocity, a needle angular body velocity, or a needle absolute speed.

12. The method of claim 1, wherein the telemetry data is obtained from sensor readings over time for at least one percutaneous needle instrument and/or at least one endoluminal scope instrument used in the prior percutaneous medical procedure, the method further comprising:

generating one or more clinical metrics associated with the first phase of the percutaneous medical procedure based on one or more case logs.

13. The method of claim 12, wherein the one or more clinical metrics includes at least one of:

a number of targeted calyces, a kidney survey time, a retraction distance, a parked pose, a site selection time, an average tract length, an anatomical angle, a field generator distance, a relative needle to scope angle, a tract length, or an angle to a calyx.

14. The method of claim 12, wherein the one or more clinical metrics includes at least one of:

a success rate, a needle insertion accuracy, a needle insertion stability, a shift in a scope position, an accuracy, a number of attempts, a needle insertion speed, a needle retraction speed, a needle insertion acceleration, or a needle retraction acceleration.

15. The method of claim 12, further comprising:

generating an indication as to whether the percutaneous medical procedure is likely to be successful based on the one or more clinical metrics associated with the first phase of the percutaneous medical procedure.

16. The method of claim 15, further comprising:

generating a guidance for the percutaneous medical procedure or a subsequent percutaneous medical procedure based on the indication.

17. The method of claim 16, wherein the guidance includes at least one of:

an indication of a needle insertion site or an indication of a needle trajectory.

18. The method of claim 1, wherein the first phase represents at least one of:

a target selection phase, a site selection phase, a needle insertion phase, or a post needle insertion phase.

19. A system for segmenting a percutaneous medical procedure, the system comprising:

a control system configured to:

obtain a first set of features over a first time period, the first set of features being derived from scope telemetry data corresponding to an endoluminal scope instrument;

obtain a second set of features over the first time period, the second set of features being derived from needle telemetry data corresponding to a percutaneous needle instrument; and classify at least one portion of the first time period as a first phase of the percutaneous medical procedure based on the first set of features, the second set of features, and telemetry data received from a medical system while performing a prior percutaneous medical procedure on a physical anatomy.

20. A method of segmenting a percutaneous medical procedure based on one or more determinable phases, the method comprising:

obtaining a first set of features over a first time period, the first set of features being derived from scope telemetry data corresponding to an endoluminal scope instrument;

obtaining a second set of features over the first time period, the second set of features being derived from needle telemetry data corresponding to a percutaneous needle instrument; and classifying at least one portion of the first time period as a first phase of the percutaneous medical procedure based on the first set of features, the second set of features, and telemetry data received from a medical system while performing a prior percutaneous medical procedure on a physical anatomy, wherein classifying the at least one portion of the first time period includes:

indicating a beginning of an attempt to insert the percutaneous needle instrument towards a target location through a percutaneous entrance; and indicating an end of the attempt to insert the percutaneous needle instrument towards the target location through the percutaneous entrance.

\* \* \* \* \*